United States Patent
Olsen et al.

(10) Patent No.: US 6,428,978 B1
(45) Date of Patent: Aug. 6, 2002

(54) METHODS FOR THE PRODUCTION OF GELATIN AND FULL-LENGTH TRIPLE HELICAL COLLAGEN IN RECOMBINANT CELLS

(75) Inventors: David R. Olsen, Menlo Park; Robert Chang, Hillsborough; Hugh McMullin, Menlo Park; Ronald A. Hitzeman, Pacifica; George Chisholm, San Mateo, all of CA (US)

(73) Assignees: Cohesion Technologies, Inc., Palo Alto; Genotypes, Inc., Pacifica, both of CA (US)

( * ) Notice: Subject to any disclaimer, the term of this patent is extended or adjusted under 35 U.S.C. 154(b) by 0 days.

(21) Appl. No.: 09/289,578

(22) Filed: Apr. 9, 1999

Related U.S. Application Data

(60) Provisional application No. 60/084,828, filed on May 8, 1998.

(51) Int. Cl.$^7$ .......................... C12P 21/06; C07H 21/02; C07H 21/04; C07K 14/00
(52) U.S. Cl. ..................... 435/69.1; 536/23.1; 536/24.3; 530/350; 530/354; 530/356
(58) Field of Search ................................ 530/350, 354, 530/356; 435/325, 243; 935/66

(56) References Cited

U.S. PATENT DOCUMENTS

| | | | |
|---|---|---|---|
| 5,002,071 A | | 3/1991 | Harrell |
| 5,256,418 A | * | 10/1993 | Kemp et al. ................. 424/423 |
| 5,328,955 A | * | 7/1994 | Rhee et al. ................. 525/54.1 |
| 5,428,022 A | | 6/1995 | Palefsky et al. |
| 5,496,712 A | | 3/1996 | Capello et al. |
| 5,593,859 A | | 1/1997 | Prockop et al. |
| 5,663,482 A | | 9/1997 | Prockop et al. |
| 5,667,839 A | | 9/1997 | Berg |
| 5,714,582 A | * | 2/1998 | Wolfinbarger ................ 530/356 |
| 5,731,417 A | * | 3/1998 | Swiderek et al. ............ 530/356 |
| 5,807,981 A | * | 9/1998 | Brenner ....................... 530/327 |
| 5,830,708 A | * | 11/1998 | Naughton ................... 435/70.1 |
| 5,962,639 A | * | 10/1999 | Eyre .......................... 530/329 |
| 6,020,193 A | * | 2/2000 | Prockop et al. ........... 435/320.1 |
| 6,037,139 A | * | 3/2000 | Greenspan et al. ............ 435/23 |
| 6,096,309 A | * | 8/2000 | Prior et al. ............... 424/94.63 |

FOREIGN PATENT DOCUMENTS

| WO | WO 97/08331 | 3/1997 |
|---|---|---|
| WO | WO 97/14431 | 4/1997 |

OTHER PUBLICATIONS

Sicot et al., European Journal of Biochemistry 246(1) : 50–58 ( May 1997).*
Su et al., Geniomics 4 (3) : 438–441 (1989).*
Ala–Kokko et al. (1991). "Expression of a Human Cartilage Porcollogen Gene (COL2A1) in Mouse 3T3 Cells," *J. Biol. Chem.* 266(22):14175–14178.

Ala–Kokko et al., (1989), "Structure of cDNA Clones Coding for the Entire Prepro α1 (III) Chain of Human Type III Procollagen. Differences in Protein Structure From Type I Procollagen and Conservation of Codon Perferences," *Biochem. J.* 260(2):509–516.

Arnold et al. (1997), "A cDNA Cassette System for the Synthesis of Recombinant Procollagens. Variants of Procollagen II Lacking a D–Period are Secreted as Triple–Helical Monomers," *Matrix Biol.* 16:105–116.

Arnold et al. "Circular Dichroism Analysis of Novel Recombinant Type II Procollagens." *Sixth International Conference on the Molecular Biology and Pathology of Matrix*: 153.

Ausubel et al., Current Protocols in Molecular Biology (Green Publishing and Wiley–Interscience: New York, 1987 (Table of Contents).

Bachinger et al., (1980), "Folding Mechanism of the Triple Helix in Type–III Collagen and Type–III pN–Collagen. Role of Disulfide Bridges and Peptide Bond Isomerization," *Eur. J. Biochem.*, 106:619–632.

Bachinger et al., (1981), "Chain Assembly Intermediate in the Biosynthesis of Type III Procollagen in Chick Embryo Blood Vessels," *J. Biol. Chem.* 256:13193–13199.

Bassuk et al., (1989), "Prolyl 4–Hydroxylase: Molecular Cloning and the Primary Structure of the α Subunit from Chicken Embryo," *Proc. Natl. Acad. Sci. USA* 86:7382–7386.

Bernard et al., (1988), "Cloning and Sequencing of Proα1 (XI) Collagen cDNA Demonstrates that Type XI Belongs to the Fibrillar Class of Collagens and Reveals that the Expression of the Gene is not Restricted to Cartilagenous Tissue," *J. Biol. Chem.* 263(32):17159–17166.

Bole et al. "Expression of Human Collagen α1(I) Chains in COS 7 Cells," *Collagen and Related Proteins: Expression and Biochemistry* Abstract No. 427: A444.

Bonaldo et al. (1990). "Efficient Expression of Chicken α 1(VI) Collagen Chain in Transiently Transfected Mammalian Cells," *Matrix* 10:139–147.

Broker, (1994), "Isolation of Recombinant Proteins from *Saccharomyces cerevisiae* by Use of Osmotically Fragile Mutant Strains," *Biotechniques* 16:604–615.

Bruckner et al. (1978). "Three Conformationally Distinct Domains in the Amino–Terminal Segment of Type III Collagen and its Rapid Triple Helix to Coil Transition," *Eur. J. Biochem.* 90: 595–603.

Bruckner et al. (1981), "Proteolytic Enzymes as Probes for the Triple–Helical Conformation of Procollagen," *Anal. Biochem.* 110:360–368.

(List continued on next page.)

Primary Examiner—Ethan C. Whisenant
(74) Attorney, Agent, or Firm—Richard Aron Osman

(57) ABSTRACT

Methods are disclosed for simplified recombinant production of fibrillar collagens. DNAs encoding fibrillar collagen monomers lacking the N propeptide, the C propeptide, or both propeptides are introduced into recombinant host cells and expressed. Trimeric collagen is recovered from the recombinant host cells.

31 Claims, 14 Drawing Sheets

OTHER PUBLICATIONS

Bulleid et al., (1997), "The C–Propetptide Domain of Procollagen can be Replaced with a Transmembrane Domain Without Affecting Trimer Formation or Collagen Triple Helix Folding During Biosynthesis," *EMBO J.* 16(22):6694–6701.

Colombatti et al. "Secretion and Matrix Assembly of Recombinant Type VI Collagen," (abstract) *Fifth International Conference on the Molecular Biology and Pathology of Matrix*: p. 358.

Colombatti et al. "Stable Expression of Chicken Type VI Collagen α1, α2 and α3 cDNAs in Murine NIH/3T3 Cells," (abstract) *Fourth International Conference on the Molecular Biology and Pathology of Matrix.* :p. 8.

Doege et al. (1986). "Folding of Carboxyl Domain and Assembly of Procollagen I," *J. Biol. Chem.* 261(19): 824–8935.

Fertala et al. (1994). "Synthesis of Recombinant Human Procollagen II in a Stably Transfected Tumour Cell Line (HT1080)," *J. Biochem* 298:31–37.

Fertala et al. (1997). "Collagen II Containing a Cys Substitution for Arg–α1–519," *J. Biol. Chem.* 272(10) 6457–6464.

Fertala et al. "Expression of Normal and Mutated Type II Procollagen Genes in Transfected Human Tumor Cells (HT–1080)," (abstract) *Fourth International Conference on the Molecular Biology and Pathology of Matrix*: p. 15.

Fichard et al. (1994). "Another Look at Collagen V and XI Molecules," *Matrix Biol.* 14:515–531.

Fichard et al. (1997). "Human Recombinant α1(V) Collagen Chain," *J. Biol. Chem.* 272(46): 30083–30087.

Fields et al. (1987). "Sequence Specificity of Human Skin Fibroblast Collagenase," *J. Biol. Chem.* 262(13):6221–6226.

Geddis et al. (1993) "Expression of Human COL1A1 Gene in Stably Transfected HT1080 Cells: The Production of a Thermostable Homotrimer of Type I Collagen in a Recombinant System," *Matrix* .13:399–405.

Greenspan et al. (1989). "High Levels of Expression of Full Length Human Pro–α2(V) Collagen cDNA in Pro–α2(V)–deficient Hamster Cells," *J. Biol. Chem.* 264(34):20683–20687.

Highberger et al. (1979). "Isolation and Characterization of a Peptide Containing the Site of Cleavage of the Chick Skin Collagen α1[1] Chain by Animal Collagenases," *Biochem. and Biophys. Res. Comm.* 89(1):202–208.

Kao et al., (1988), "Isolation of cDNA Clones and Genomic DNA Clones of β–Subunit of Chicken Prolyl 4–Hydroxylase," *Conn. Tiss. Res.* 18:157–174.

Kimura et al., (1989), "The Human α2(XI) Collagen (COL11A2) Chain," *J. Biol. Chem.* 264(23):13910–13916.

Kuivaniemi et al., (1988), "Structure of a Full–Length cDNA Clone for the Prepoα2(I) Chain of Human Type I Procollagen," *Biochem J.* 252(3):633–640.

Lamberg et al., (1996), "Charaterization of Human Type III Collagen Expressed in a Baculovirus System," *J. Biol. Chem.* 271(20):11988–11995.

Lee et al. (1988). "Construction of a Full–length cDNA Encoding Human Pro–α2(I) Collagen and Its Expression in Pro–α2(I)–deficient W8 Rat Cells," *J. Biol. Chem.* 263(26): 13414–13418.

Lee et al. (1992), "Deletion of the Pro–α(I) N–Propetide Affects Secretion of Type I Collagen in Chinese Hamster Lung Cells but not in Mov–13 Mouse Cells," *J. Biol. Chem.* 267(33):24126–24133.

Lees et al. (1994). "The Role of Cysteine Residues in the Folding and Association of the COOH–terminal Propeptide of Types I and II Procollagen," *J. Biol. Chem.* 269(39):24354–24360.

Lees et al. (1997). "Identification of the Molecular Recognition Sequence Which Determines the Type–Specific Assembly of Procollagen," *EMBO J.* 16:908–916.

Lees et al. "Molecular Signals within the C–Propeptide which Determine Type–Scientific Assembly of Procollagen Chains," (abstract) *Sixth International Conference on the Molecular Biology and Pathology of Matrix*: p. 153.

Mann, (1992), "Isolation of the α3–Chain of Human Type V Collagen and Characterization by Partial Sequencing," *Biol. Chem. Hoppe Seyler* 373:69–75.

Mazzarona et al. (1995). "Trimeric Assembly of Collagen XII: Effect of Deletion of the C–Terminal Part of Molecules," *Matrix Biol.* 14:583–588.

Mazzorana et al. "Expression of a Collagen Type XII Minigene in Transiently Transfected Hela Cells," (abstract) *Fourth International Conference on the Molecular Biology and Pathology of Matrix.*: p. 5.

Mazzorana et al., (1996)."Involvement of Prolyl 4–Hydroxylase in the Assembly of Trimeric Minicollagen XII," *J. Biol. Chem.* 271(46):29003–29008.

McLaughlin et al., (1998), "Molecular Recognition in Procollagen Chain Assembly," *Matrix Biol.* 16:369–377.

McPherson et al. (1986), "The Preparation and Physicochemical Characterization of an Injectable Form of Reconstituted, Glutaraldehyde Cross–Linked, Bovine Corium Collagen," *J. Biomed. Mat. Res.* 20:79–92).

Miller et al., (1982), "Preparation and Characterization of the Different Types of Collagen," *Meth. Enzymol.* 82:33–64.

Myllyharju et al. (1997). "Expression of Wild–Type and Modified Proα Chains of Human Type I Procollagen in Insect Cells Leads to the Formation of Stable $[\alpha 1(I)]_2 \alpha 2(I)$ Collagen Heterotrimers and $[\alpha 1(I)]_3$ Homotrimers but not $[\alpha 2(I)]_3$ Homotrimers," *J. Biol. Chem.* 272(35): 21824–21830.

Nokelainen et al. (1997). "Expression and Characterization of Recombinant Human Type II Collagens with Low and High Contents of Hydroxylysine and Its Glycosylated Forms," *Matrix Biol.* 16:329–338.

Olsen et al. (1991). "High Levels of Expression of a Minigene Version of the Human Proα1(I) Collagen Gene in Stably Transfected Mouse Fibroblasts," *J. Biol. Chem.* 266:1117–1121.

Pelletier et al., (1997), "Deletion Analysis of ors12, a Centromeric, Early Activated, Mammalian Origin of DNA Replication," *J. Cell. Biochem.* 66(1):87–97).

Romanos et al. (1992), "Foreign Gene Expression in Yeast: a Review," *Yeast* 8:423–488.

Sambrook et al., Molecular Cloning: A Laboratory Manual, vols. 1–3 (Cold Spring Harbor Laboratory Press, 2 ed., 1989 (Table of Contents).

Sandell et al., (1991), "Alternatively Spliced Type II Procollagen mRNAs Define Distinct Populations of Cells during Vertebral Development: Differential Expression of the Amino–Propeptide," *J. Cell. Biol.*, 114:1307–1319.

Sieron et al. (1993), "Deletion of a Large Domain in Recombinant Human Procollagen II Does Not Alter the Thermal Stability of the Triple Helix," *J. Biol. Chem.* 268(28):21232–21237.

Sokolov et al (1993). "Tissue– and Development–Specific Expression in Transgenic Mice of a Type I Procollagen (COL1A1) Minigene Construct with 2.3 kb of the Promoter Region and 2 kb of the 3'–Flanking Region. Specificity Is Independent of the Putative Regulatory Sequences in the First Intron," *Biochem.* 32:9242–9249.

Stacey et al. (1987). "Rescue of Type I Collagen–Deficient Phenotype by Retroviral–Vector–Mediated Transfer of Human proα1(I) Collagen Gene into Mov–13 Cells," *J. Virol.* 61(8): 2549–2554.

Su et al., (1989), "Nucleotide Sequence of the Full Length cDNA Encoding for Human Type II Collagen,"*Nucleic Acid Res.* 17(22):9473.

Takahara et al., (1991), "Complete Primary Structure of Human Collagen α1(V) Chain," *J. Biol. Chem.* 266(20):13124–13129.

Tillet et al. (1994). "Recombinant Expression and Structural and Binding Properties of α1 (VI) and α2 (VI) Chains of Human Collagen Type VI," *Eur. J. Biochem.* 221(1): 177–185.

Tomita et al. (1995). "Biosynthesis of Recombinant Human proα1 (III) Chains in a Baculovirus Expression System: Production of Disulphide–Bonded and Non–Disulphide–Bonded Species Containing Full–Length Triple Helices," *Biochem. J.* 312 (Pt 3): 847–853).

Tomita et al. (1997). "Formation of Recombinant Human Procallogen I Heterotrimers in a Baculovirus Expression System," *J. Biochem.* 121:1061–1069.

Towbin et al., (1979), "Electrophoretic Transfer of Proteins from Polyacrylamide Gels to Nitrocellulose Sheets: Procedure and Some Applications," *Proc. Natl. Acad. Sci. USA* 76:4350–4354.

Tromp et al., (1988), "Structure of a Full–Length cDNA Clone for the Preproα1(I) Chain of Human Type I Procollagen," *Biochem J.* 253(3):919–922.

Vuorela et al., (1997), "Assembly of Human Prolyl 4–Hydroxylase and Type III Collagen in the Yeast *Pichia pastoris*: Formation of a Stable Enzyme Tetramer Requires Coexpression with Collagen and Assembly of a Stable Collagen Requires Coexpression with Prolyl 4–Hydroxylase," *EMBO J* 16(22):6702–6712.

Weil et al., (1987), "The Proα2(VI) Collagen Gene is Evolutionarily Related to the Major Fibrillar–Forming Collagens," *Nucleic Acid Res.* 15(1):181–198.

Wu et al., (1990), "Generation of Collagenase–Resistant Collagen by Site–Directed Mutagenesis of Murine Proα1(I) Collagen Gene," *Proc. Natl. Acad. Sci. USA* 78:5888–5892.

Zafarullah et al. (1997). "A Recombinant Homotrimer of Type I Procollagen that Lacks the Central Two D–Periods. The Thermal Stability of the Triple Helix is Decreased by 2 to 4° C," *Matrix Biol.* 16:245–253.

Zafarullah et al. (1997). "Synthesis and Conformational Properties of a Recombinant C–Propeptide of Human Type III Procollagen," *Matrix Biol.* 16:201–209.

Becker, D.M. et al. (1991). "High–Efficiency Transformation of Yeast by Electroporation," Meth Enz 194:182–187.

Berg, R.A. et al. (1973). "The Thermal Transition of a Non–hydroxulated Form of Collagen. Evedence for a Role for Hydroxyproline in Stabilizing the Triple–Helix of Collagen," *Biochem Biophys Res Commun* 52:115–120.

Berg, R.A. et al. (1980). "Regulation of the Production of Secretory Proteins: Intracellular Degradation of Newly Synthesized "Defective" Collagen," *Proc Nat Acad Sci USA* 77:4746–4750.

Birk, D.E. et al. (1990). "Collagen Fibrillogenesis In Vitro: Interaction of Collagen Types I and V Regulates Fibril Diameter," *J Cell Sci* 95:649–657.

Birk, D.E. et al. (1995). "Collagen Fibrillogenesis In Situ: Fibril Segments Undergo Post Depositional Modification Resulting in Linear and Lateral Growth During Matrix Development," *Dev Dyn* 202:229–243.

Byrne, M.H. et al. (1992). "Sliding the Collagenase Cleavage Site in the Alph1(1) Chain Out of Phase with the α2(1) Chain Confers Collagenase Resistance," *4th Int Conf Mol Pathol Matrix*, Jun. 10–13.

Doyle, S.A. et al. (1998). "Role of the Pro–α2(1) COOH–Terminal Region in Assembly of Type 1 Collagen: Distribution of Two Intramolecular Disulfide Bonds in Pro–α2(1) Blocks Assembly of Type 1 Collagen," *J Cell Biochem* 71:233–242.

Fields, G.B. et al. (1992). "Unique Features of the Tissue Collagenase Cleavge Site in Interstitial Collagens," *Matrix Suppl* 1:68–70.

Gelman, R.A. et al. (1979). "Collagen Fibril Formation In Vitro. The Role of the Nonhelical Terminal Regions," *J Biol Chem* 254:11741–11745.

Highberger, J.J. (1979). "Isolation and Characterization of a Peptide Containing the Site of Cleavage of Chick Skin Collagen by Animal Colagenases," *Biochem Biophys Res Commun* 89:202–208.

Hitzeman, R.A. et al. (1990). "Use of Heterologuos and Homologuos Signal Sequences for Secretion of Heterologuos Proteins from Yeast," Meth Enz 185:421–441.

Kadler, K. (1995). "Extracellular Matrix 1: Fibril–Forming Collagens," *Protein Profile* 2:491–619.

Kao, K. et al. (1977). "Kinetics of the Secretion of Procollagen by Freshly Isolated Tendom Cells," *J Biol Chem* 252:8391–8397.

Kao, K. et al. (1979). "Kinetics of the Secretion of Nonhelical Procollagen by Freshly Isolated Tendom Cells," *J Biol Chem* 254:2234–2243.

Kiviriko, K.I. et al. (1989). "Prolyl 4–Hydroxylase, an Enzyme with Four Cosubstrates and a Multifunctional Subunit," *FASEB J* 3:1609–1617.

Lim, A.–L. et al. (1998). "Role of the Pro–α2(1) COOH–Terminal Region in Assembly of Type 1 Collagen: Truncation of the Last 10 Aminoacid Residues of Pro–α2(1) Chain Prevents Assembly of Type 1 Collagen Heterotrimer," *J Cell Biochem* 71:216–232.

McLaughlin, S.H. et al. (1997). "Molecular Recognition in Procollagen Chain Assembly," *Matrix Biol* 16:369–377.

McPherson, J.M. et al. (1985). "Collagen Fibrillogenesis In Vitro: A Characterization of Fibril Quality as a Function of Assembly Conditions," *Collagen Rel Res* 5:119–135.

Prockop, D.J. et al. (1998). "The Collagen Fibril: the Almost Crystalline Structure," *J Struct Biol* 122:11–118.

Rosenbloom, J. et al. (1976). "Termination of Procollagen Chain Synthesis by Puromycin: Evidence that Assembly and Secretion Require a COOH–Terminal Extension," *J Biol Chem* 251: 2070–2076.

Schofield, D.J. et al. (1974). "Formation of Interchain Disulfide Bonds and Helical Structure During Biosynthesis of Procollagen by Embryonic Tendon Cells," *Biochem* 13:1801–1806.

Toman, P.D. et al. "Production of Recombinant Human Type 1 Procollagen in the Yeast *Saccharomyces cerevisiae*," *J Biol Chem* 275(30:23303–23309.

Uitto, J. et al. (1974). "Incorporation of Proline Analogs into Collagen Polypeptides. Effects on he Production of Extracellular Procollagen and on the Stability of the Triple Helical Structure of the Molecule," *Biochem Biophys Acta* 336:234–251.

Uitto, V. et al. (1981). "Synthesis of type 1 Procollagen: Formation of Interchain Disulfide Bonds Before Complete Hydroxylation of the Protein," *Arch Biochem Biophys* 210:440–445.

Vaughan, P.R. et al. (1998). "Productuin of Recombinant Hydroxylated Human Type 111 Collagen Fragment in *Saccaromyces cerevisia*," *DNA Cell Biol* 17:511–518.

* cited by examiner

FIG. 1

| Monomer | 1                                    23 |
|---------|------------------------------------------|
| α1(I)   | GGQGSDPADVAIQLTFLRLMSTE                  |
| α2(I)   | NVEGVTSKEMATQLAFMRLLANY                  |
| α1(II)  | GDDNLAPNTANVQMTFLRLLSTE                  |
| α1(III) | FNPELPEDVLDVQLAFLRLLSSR                  |
| α1(V)   | VDAEFNPVGV VQMTGLRLLSAS                  |
| α2(V)   | GDHQSPNTAI TQMTFLRLLSKE                  |
| α1(XI)  | LDVEGNSINM VQMTFLKLLTAS                  |
| α2(XI)  | VDSEGSPVGV VQLTFLRLLSVS                  |

FIG. 3A

```
1                                                                    50
MFSFVDLRLL LLLAATALLT HGQEEGQVEG QDEDIPPITC VQNGLRYHDR 51                                                                  100
DVWKPEPCRI CVCDNGKVLC DDVICDETKN CPGAEVPEGE CCPVCPDGSE 101                                                                 150
SPTDQETTGV EGDTGPRGPR GPAGPPGRDG IPGQPGLPGP PGPPGPPGPP

151      *                                                          200
GLGGNFAPQL SYGYDEKSTG GISVPGPMGP SGPRGLPGPP GAPGPQGFQG 201                                                                 250
PPGEPGEPGA SGPMGPRGPP GPPGKNGDDG EAGKPGRPGE RGPPGPQGAR 251                                                                 300
GLPGTAGLPG MKGHRGFSGL DGAKGDAGPA GPKGEPGSPG ENGAPGQMGP 301                                                                 350
RGLPGERGRP GAPGPAGARG NDGATGAAGP PGPTGPAGPP GFPGAVGAKG 351                                                                 400
EAGPQGPRGS EGPQGVRGEP GPPGPAGAAG PAGNPGADGQ PGAKGANGAP 401                                                                 450
GIAGAPGFPG ARGPSGPQGP GGPPGPKGNS GEPGAPGSKG DTGAKGEPGP 451                                                                 500
VGVQGPPGPA GEEGKRGARG EPGPTGLPGP PGERGGPGSR GFPGADGVAG 501                                                                 550
PKGPAGERGS PGPAGPKGSP GEAGRPGEAG LPGAKGLTGS PGSPGPDGKT 551                                                                 600
GPPGPAGQDG RPGPPGPPGA RGQAGVMGFP GPKGAAGEPG KAGERGVPGP 601                                                                 650
PGAVGPAGKD GEAGAQGPPG PAGPAGERGE QGPAGSPGFQ GLPGPAGPPG 651                                                                 700
EAGKPGEQGV PGDLGAPGPS GARGERGFPG ERGVQGPPGP AGPRGANGAP 701                                                                 750
GNDGAKGDAG APGAPGSQGA PGLQGMPGER GAAGLPGPKG DRGDAGPKGA 751                                                                 800
```

FIG. 3B

```
     DGSPGKDGVR GLTGPIGPPG PAGAPGDKGE SGPSGPAGPT GARGAPGDRG 801                                                      850
     EPGPPGPAGF AGPPGADGQP GAKGEPGDAG AKGDAGPPGP AGPAGPPGPI 851                                                      900
     GNVGAPGAKG ARGSAGPPGA TGFPGAAGRV GPPGPSGNAG PPGPPGPAGK 901                                                      950
     EGGKGPRGET GPAGRPGEVG PPGPPGPAGE KGSPGADGPA GAPGTPGPQG 951                                                     1000
     IAGQRGVVGL PGQRGERGFP GLPGPSGEPG KQGPSGASGE RGPPGPMGPP 1001                                                    1050
     GLAGPPGESG REGAPGAEGS PGRDGSPGAK GDRGETGPAG PPGAPGAPVA 1051                                                    1100
     PGPVGPAGKS GDRGETGPAG PAGPVGPVGA RGPAGPQGPR GDKGETGEQG 1101                                                    1150
     DRGIKGHRGF SGLQGPPGPP GSPGEQGPSG ASGPAGPRGP PGSAGAPGKD 1151                                                    1200
     GLNGLPGPIG PPGPRGRTGD AGPVGPPGPP GPPGPPGPPS AGFDFSFLPQ

1201              #                                     1250
     PPQEKAHDGG RYYRADDANV VRDRDLEVDT TLKSLSQQIE NIRSPEGSRK 1251                                                    1300
     NPARTCRDLK MCHSDWKSGE YWIDPNQGCN LDAIKVFCNM ETGETCVYPT 1301                                                    1350
     QPSVAQKNWY ISKNPKDKRH VWFGESMTDG FQFEYGGQGS DPADVAIQLT 1351                                                    1400
     FLRLMSTEAS QNITYHCKNS VAYMDQQTGN LKKALLLKGS NEIEIRAEGN 1401                                                    1450
     SRFTYSVTVD GCTSHTGAWG KTVIEYKTTK TSRLPIIDVA PLDVGAPDQE 1460      1461
     FGFDVGPVCF L
```

FIG. 4A

```
1                                                                    50
MLSFVDTRTL LLLAVTLCLA TCQSLQEETV RKGPAGDRGP RGERGPPGPP

51                              *                                   100
GRDGEDGPTG PPGPPGPPGP PGLGGNFAAQ YDGKGVGLGP GPMGLMGPRG 101                                                                 150
PPGAAGAPGP QGFQGPAGEP GEPGQTGPAG ARGPAGPPGK AGEDGHPGKP 151                                                                 200
GRPGERGVVG PQGARGFPGT PGLPGFKGIR GHNGLDGLKG QPGAPGVKGE 201                                                                 250
PGAPGENGTP GQTGARGLPG ERGRVGAPGP AGARGSDGSV GPVGPAGPIG 251                                                                 300
SAGPPGFPGA PGPKGEIGAV GNAGPAGPAG PRGEVGLPGL SGPVGPPGNP 301                                                                 350
GANGLTGAKG AAGLPGVAGA PGLPGPRGIP GPVGAAGATG ARGLVGEPGP 351                                                                 400
AGSKGESGNK GEPGSAGPQG PPGPSGEEGK RGPNGEAGSA GPPGPPGLRG 401                                                                 450
SPGSRGLPGA DGRAGVMGPP GSRGASGPAG VRGPNGDAGR PGEPGLMGPR 451                                                                 500
GLPGSPGNIG PAGKEGPVGL PGIDGRPGPI GPAGARGEPG NIGFPGPKGP 501                                                                 550
TGDPGKNGDK GHAGLAGARG APGPDGNNGA QGPPGPQGVQ GGKGEQGPAG 551                                                                 600
PPGFQGLPGP SGPAGEVGKP GERGLHGEFG LPGPAGPRGE RGPPGESGAA 601                                                                 650
GPTGPIGSRG PSGPPGPDGN KGEPGVVGAV GTAGPSGPSG LPGERGAAGI 651                                                                 700
PGGKGEKGEP GLRGEIGNPG RDGARGAHGA VGAPGPAGAT GDRGEAGAAG 701                                                                 750
PAGPAGPRGS PGERGEVGPA GPNGFAGPAG AAGQPGAKGE RGAKGPKGEN 751                                                                 800
```

FIG. 4B

```
          GVVGPTGPVG AAGPAGPNGP PGPAGSRGDG GPPGMTGFPG AAGRTGPPGP
801                                                          850
          SGISGPPGPP GPAGKEGLRG PRGDQGPVGR TGEVGAVGPP GFAGEKGPSG
851                                                          900
          EAGTAGPPGT PGPQGLLGAP GILGLPGSRG ERGLPGVAGA VGEPGPLGIA
901                                                          950
          GPPGARGPPG AVGSPGVNGA PGEAGRDGNP GNDGPPGRDG QPGHKGERGY
951                                                         1000
          PGNIGPVGAA GAPGPHGPVG PAGKHGNRGE TGPSGPVGPA GAVGPRGPSG
1001                                                        1050
          PQGIRGDKGE PGEKGPRGLP GLKGHNGLQG LPGIAGHHGD QGAPGSVGPA
1051                                                        1100
          GPRGPAGPSG PAGKDGRTGH PGTVGPAGIR GPQGHQGPAG PPGPPGPPGP
1101                    #                                   1150
          PGVSGGGYDF GYDGDFYRAD QPRSAPSLRP KDYEVDATLK SLNNQIETLL
1151                                                        1200
          TPEGSRKNPA RTCRDLRLSH PEWSSGYYWI DPNQGCTMDA IKVYCDFSTG
1201                                                        1250
          ETCIRAQPEN IPAKNWYRSS KDKKHVWLGE TINAGSQFEY NVEGVTSKEM
1251                                                        1300
          ATQLAFMRLL ANYASQNITY HCKNSIAYMD EETGNLKKAV ILQGSNDVEL
1301                                                        1350
          VAEGNSRFTY TVLVDGCSKK TNEWGKTIIE YKTNKPSRLP FLDIAPLDIG
1351                1366
          GADHEFFVDI GPVCFK
```

METHODS FOR THE PRODUCTION OF GELATIN AND FULL-LENGTH TRIPLE HELICAL COLLAGEN IN RECOMBINANT CELLS

This application claims priority under 35 USC §119(e) to U.S. Provisional Application Serial No. 60/084,828, filed May 8, 1998, the contents of which is incorporated herein in its entirety.

TECHNICAL FIELD

The invention relates generally to the field of recombinant protein production, and particularly to the production of telopeptide collagen in recombinant host cells.

BACKGROUND ART

Collagen is the major protein component of bone, cartilage, skin and connective tissue in animals. Collagen in its native form is typically a rigid, rod-shaped molecule approximately 300 nm long and 1.5 nm in diameter. It is composed of three collagen polypeptide monomers which form a triple helix. Mature collagen monomers are characterized by a long midsection having the repeating sequence —Gly-X-Y, where X and Y are often proline or hydroxyproline, bounded at each end by the "telopeptide" regions, which constitute less than about 5% of the molecule. The telopeptide regions of the chains are typically responsible for the crosslinking between the chains (i. e., the formation of collagen fibrils), and for the immunogenicity of the protein. Collagen occurs naturally in a number of "types", each having different physical properties. The most abundant types in mammals and birds are types I, II and III.

Mature collagen is formed by the association of three procollagen monomers which include "pro" domains at the amino and carboxy terminal ends of the polypeptides. The pro domains are cleaved from the assembled procollagen trimer to create mature, or "telopeptide" collagen. The telopeptide domains may be removed by chemical or enzymatic means to create "atelopeptide" collagen.

Interestingly, although there are a large number of different genes encoding for different procollagen monomers, only particular combinations are produced naturally. For example, skin fibroblasts synthesize 10 different procollagen monomers (proα1(I), proα1(III), proα1(V), proα2(I), proα2(V), proα3(V), proα1(VI), proα2(VI), proα3(VI) and proα1(VII)), but only 5 types of mature collagen are produced (types I, III, V, VI and VII).

Collagen has been utilized extensively in biological research as a substrate for in vitro cell culture. It has also been widely used as a component of biocompatible materials for use in prosthetic implants, sustained drug release matrices, artificial skin, and wound dressing and wound healing matrices.

Historically, collagen has been isolated from natural sources, such as bovine hide, cartilage or bones, and rat tails. Bones are usually dried, defatted, crushed, and demineralized to extract collagen, while cartilage and hide are typically minced and digested with proteolytic enzymes other than collagenase. As collagen is resistant to most proteolytic enzymes (except collagenase), this procedure can conveniently remove most of the contaminating protein that would otherwise be extracted along with the collagen. However, for medical use, species-matched collagen (e.g., human collagen for use in human subjects) is highly desirable in order to minimize the potential for immune response to the collagen material.

Human collagen may be purified from human sources such human placenta (see, for example, U.S. Pat. Nos. 5,002,071 and 5,428,022). Of course, the source material for human collagen is limited in supply and carries with it the risk of contamination by pathogens such as hepatitis virus and human immunodeficiency virus (HIV). Additionally, the material recovered from placenta is biased as to type and not entirely homogenous.

Collagen may also be produced by recombinant methods. For example, International Patent Application No. WO 97/14431 discloses methods for recombinant production of procollagen in yeast cells and U.S. Pat. No. 5,593,859 discloses the expression of procollagen genes in a variety of cell types. In general, the recombinant production of collagen requires a cloned DNA sequence encoding the appropriate procollagen monomer(s). The procollagen gene(s) is cloned into a vector containing the appropriate DNA sequences and signals for expression of the gene and the construct is introduced into the host cells. Optionally, genes expressing a prolyl-4-hydroxylase alpha subunit and a protein disulfide isomerase are also introduced into the host cells (these are the two subunits which make up prolyl-4-hydroxylase). Addition of the prolyl-4-hydroxylase leads to the conversion of some of the prolyl residues in the procollagen chains to hydroxyproline, which stabilize the triple helix and increase the thermal stability of the protein.

Alternately, recombinant collagen may be produced using transgenic technology. Constructs containing the desired collagen gene linked to the appropriate promoter/enhancer elements and processing signals are introduced into embryo cells by the formation of ES cell chimera, direct injection into oocytes, or any other appropriate technique. Transgenic production of recombinant collagen is particularly advantageous when the collagen is expressed in milk (i.e., by mammary cells), such as described in U.S. Pat. No. 5,667,839 to Berg. However, the production of transgenic animals for commercial production of collagen is a long and expensive process.

One difficulty of recombinant expression of collagen is the processing of the "pro" regions of procollagen monomers. It is widely accepted that folding of the three monomers to form the trimer begins in the carboxyl pro-region ("C propeptide") and that the C propeptide contains signals responsible for monomer selection (Bachinger et al., 1980, *Eur. J Biochem.*, 106:619–632; Bachinger et al., 1981, *J. Biol. Chem.* 256:13193–13199). One group has identified a region in the carboxy pro-region that they believe is necessary and sufficient for monomer selection (Bulleid et al., 1997, *EMBO J.* 16(22):6694–6701; Lees et al., 1997, *EMBO J.* 16(5):908–916; International Patent Application No. WO 97/0831 1; McLaughling et al., 1998, *Matrix Biol.* 16:369–377). Additionally, Lee et al. (1992, *J. Biol. Chem.* 267(33):24126–24133) have shown that deletion of the N propeptide results in decreased secretion of human α1 pC collagen from CHL cells, but not Mov-13 cells. Accordingly, it is believed that the pro-regions must be retained for proper chain selection, alignment and folding of collagen produced by recombinant methods. In cells which normally produce collagens, specific proteolytic processing enzymes are produced which remove the N and C propeptides following the secretion of collagen. These enzymes are not present in cells which do not normally produce procollagen (including commonly used recombinant host cells such as bacteria and yeast).

Ideally, the recombinant production of collagen is accomplished with a recombinant host cell system that has a high capacity and a relatively low cost (such as bacteria or yeast).

Because bacteria and yeast do not normally produce the enzyme necessary for processing of the N and C propeptides, the propeptides must be removed after recovering the recombinant procollagen from the host cells. This can be accomplished by the use of pepsin or other proteolytic enzymes such as PRONASE® or trypsin, but in vitro processing produces "ragged" ends that do not correspond to the ends of mature collagen secreted by mammalian cells which normally produce fibrillar collagen. Alternately, the enzymes which process the N and C propeptides can be produced and used to remove the propeptides. Any contamination of these enzyme preparations with other proteases will result in ragged ends. This added processing step increases the cost and decreases the convenience of production in these otherwise desirable host cell systems.

Gelatin can be considered a collagen derivative. Gelatin is denatured collagen, generally in monomeric form, which may be fragmented as well. Gelatin serves a large number of uses, particularly in foodstuffs as well as in medicine, where it is frequently used for coating tablets or for making capsules. However, the possibility of the spread of prion-based diseases through animal-derived gelatin has made the use of animal-derived gelatin less attractive.

Accordingly, there is a need in the art for simplified methods of producing gelatin and genuine telopeptide collagen in high capacity systems.

DISCLOSURE OF THE INVENTION

The inventors have discovered new methods for the recombinant production of fibrillar collagens. The inventors have surprisingly and unexpectedly found that co-expression of DNA constructs encoding α1(I) and α2(I) collagen monomers lacking the N and C propeptides form heterotrimeric telopeptide collagen having the properties of genuine human type I collagen. Additionally, co-expression in yeast of DNA constructs encoding a non-collagen signal sequence linked to α1(I) and α2(I) collagen monomers lacking the N, the C, or both the N and C propeptides results in a surprising increase in the production of type I collagen. Further, the inventors have found that the efficient production of triple helical fibrillar collagen in accordance with the invention is not dependent on hydroxylation of the collagen monomers.

The methods of the instant invention may be used to produce any of the fibrillar collagens (e.g., types I–III, V and XI), as well as the corresponding types of gelatin, from any species, but are particularly useful for the production of recombinant human collagens for use in medical applications. Collagen produced in accordance with the invention may be hydroxylated (i.e., proline residues altered to hydroxyproline by the action of prolyl-4-hydroxylase) or non-hydroxylated. Additionally, the methods of the invention also provide efficient methods for production of recombinant gelatin.

In one embodiment, the invention relates to methods for producing fibrillar collagen by culturing a recombinant host cell comprising a DNA encoding a fibrillar collagen monomer lacking a C propeptide sequence selection and alignment domain (SSAD) under conditions appropriate for expression of said DNA; and producing fibrillar collagen. The DNA may encode any of the fibrillar collagen monomers, such as α1(I), α2(I), α1(II), α1(III), α1(V), α2(V), α3(V), α1(XI), α2(XI), and α3(XI). Optionally, the DNA encoding the fibrillar collagen monomer lacking a C propeptide SSAD may also lack DNA encoding the N propeptide.

In another embodiment, the invention relates to methods for producing fibrillar collagen by culturing a recombinant yeast host cell comprising a DNA encoding a fibrillar collagen monomer lacking a N propeptide under conditions appropriate for expression of said DNA; and producing fibrillar collagen.

Another embodiment relates to recombinant host cells comprising an expression construct comprising a DNA encoding a fibrillar collagen monomer lacking a C propeptide sequence selection and alignment domain (SSAD). The DNA may encode any of the fibrillar collagen monomers, such as α1(I), α2(I), α1(II), α1(III), α1(V), α2(V), α3(V), α1(XI), α2(XI), and α3(XI). Optionally, the DNA encoding the fibrillar collagen monomer lacking a C propeptide SSAD may also lack DNA encoding the N propeptide.

In a further embodiment, the invention relates to trimeric collagen molecules which lack propeptide domains and lack native glycosylation and trimeric collagen molecules which lack propeptide domains and lack any glycosylation. The trimeric collagens of the invention have "genuine" ends (i.e., the amino and carboxy-terminal residues which would be produced by normal processing in tissues which naturally produce collagen).

Another embodiment of the invention relates to the production of recombinant gelatin. Gelatin may be produced using constructs encoding any collagen monomer, preferably lacking the C propeptide domain and/or the N propeptide domain in a recombinant host cell. The collagen monomers thus produced may be hydroxylated (e.g., produced in a cell with prolyl-4-hydroxylase activity) or non-hydroxylated. After collection and any purification, the collagen monomers are denatured as necessary to form gelatin, although non-hydroxylated collagen monomers expressed in host cells incubated at elevated temperatures may not require any further treatment to form gelatin.

BRIEF DESCRIPTION OF THE DRAWINGS

FIG. 1 shows an alignment of SSAD sequences, shown in single letter amino acid code (SEQ ID NO:1–8), as identified by Lees et al. (1997, supra). Positions 1–12 and 21–23 are considered the essential positions in the SSAD.

FIG. 3A and FIG. 3B show the amino acid sequence of human preproα1(I) collagen (SEQ ID NO:9) posted to Genbank under accession number AF017178. The signal sequence (pre domain) is underlined. The first amino acid of the N telopeptide is marked with an "*". The last amino acid of the C telopeptide is marked with a "#".

FIG. 4A and FIG. 4B show the amino acid sequence of human preproα2(I) collagen (SEQ ID NO:10) posted to Genbank under accession number Z74616. The signal sequence (pre domain) is underlined. The first amino acid of the N telopeptide is marked with an "*". The last amino acid of the C telopeptide is marked with a "#".

BEST MODE FOR CARRYING OUT THE INVENTION

Figure 2:
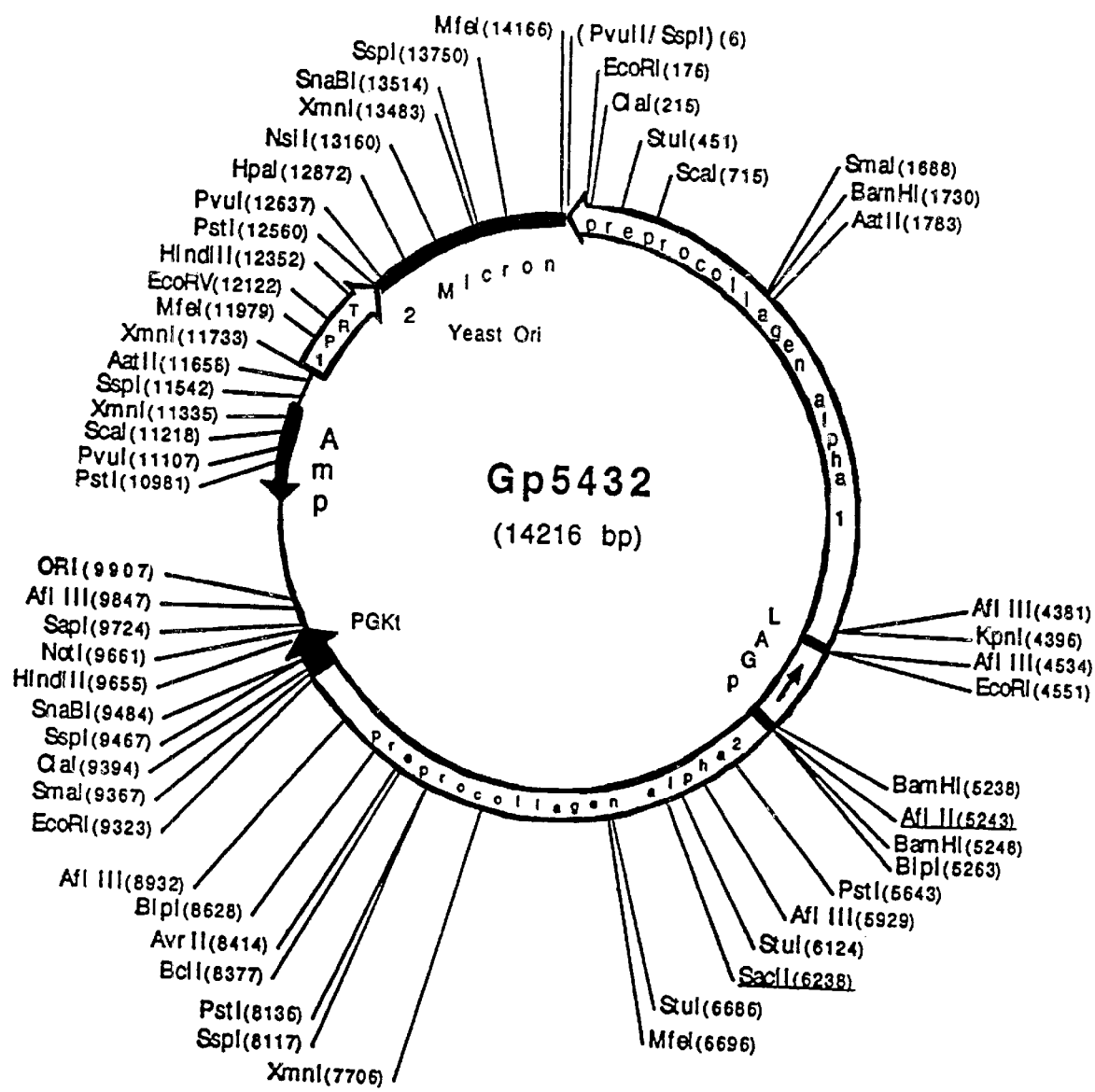
FIG. 2 shows a map of shuttle vector plasmid Gp5432.

The methods of the instant invention generally involve the use of recombinant host cells comprising DNA expression constructs encoding the production of fibrillar collagen monomers lacking at least portions of one or both of the propeptides. The recombinant host cells are incubated under conditions appropriate for the expression of the constructs, and trimeric telopeptide collagen is recovered.

Definitions

As used herein, the term "collagen" refers to a family of homotrimeric and heterotrimeric proteins comprised of collagen monomers. There are a multitude of known collagens (at least 19 types) which serve a variety of functions in the body. There are an even greater number of collagen monomers, each encoded by a separate gene, that are necessary to make the different collagens. The most common collagens are types I, II, and III. Collagen molecules contain large areas of helical structure, wherein the three collagen monomers form a triple helix. The regions of the collagen monomers in the helical areas of the collagen molecule generally have the sequence G-X-Y, where G is glycine and X and Y are any amino acid, although most commonly X and Y are proline and/or hydroxyproline. Hydroxyproline is formed from proline by the action of prolyl-4-hydroxylase, and is believed to contribute to the thermal stability of trimeric fibrillar collagen. The term "collagen", as used herein, may refer to hydroxylated fibrillar collagen (i.e., collagen containing hydroxyproline) or non-hydroxylated fibrillar collagen (i.e., collagen without hydroxyproline).

As used herein, the term "fibrillar collagen" means a collagen of a type which can normally form collagen fibrils. The fibrillar collagens are collagen types I–III, V, and XI. The collagen monomers that make up the fibrillar collagens contain "telopeptide" regions at the amino (N) and carboxy (C) terminal ends of the monomers which are non-helical in the collagen trimer. These collagens self-assemble into fibrils with the C-terminal end of the helical domain and the C propeptide of one collagen triple helix overlapping with the N telopeptide and the N-terminal end of the triple helical domain of an adjacent collagen molecule. The monomers that make up the fibrillar collagens are made as preproproteins, including an N-terminal secretion signal sequence and N and C-terminal propeptide domains. The signal sequence is normally cleaved by signal peptidase, as with most secreted proteins, and the propeptides are removed by specific proteolytic processing enzymes after association, folding and secretion of trimeric procollagen. The term fibrillar collagen encompasses both native (i.e., naturally occurring) and variant fibrillar collagens (i.e., fibrillar collagens with one or more alterations in the sequence of one or more of the fibrillar collagen monomers). Unless the context clearly indicates otherwise (e.g., the term is modified by the word "monomer") "fibrillar collagen" refers to triple helical fibrillar collagen.

The term "pC" refers to a fibrillar collagen (monomer or triple helical, trimeric molecule) which lacks a collagen N propeptide.

The term "pN" refers to a fibrillar collagen (monomer or triple helical, trimeric molecule) which lacks a collagen C propeptide.

The term "gelatin" refers to compositions comprising non-helical collagen monomers or fragments thereof. The collagen monomers may be fibrillar collagen monomers or non-fibrillar collagen monomers. Additionally, the collagen monomers (fibrillar or non-fibrillar) may be hydroxylated or non-hydroxylated.

A "heterologous prepro sequence" refers to an amino acid sequence derived from a protein other than a collagen which functions as a prepro sequence in its normal setting. A heterologous prepro sequence may include sequences not found in association with the heterologous prepro sequence in its natural setting, such as a protease recognition site sequence. A preferred example of a preferred heterologous prepro sequence is the prepro sequence from human serum albumin, which includes at its carboxy terminal end the amino acid sequence Arg-Arg, which is a KEX2 recognition site.

The term "sequence selection and alignment domain" or "SSAD" refers to a portion of the C propeptide of fibrillar collagens identified by Lees et al. (1997, supra) as responsible for chain selection and alignment. SSAD sequences for α1(I), α2(II), α1(II), α1(III), α1(V), α2(V), α1(XI), and α2(XI) have been identified in Lees et al. and are shown in FIG. 1. Only positions 1–12 and 21–23 of the sequences shown in FIG. 1 are considered part of the SSAD. SSADs from other fibrillar collagen monomers can easily be identified in the C propeptide of fibrillar collagen monomers by sequence similarity alignment with the SSADs shown in FIG. 1.

The term "DNA encoding a fibrillar collagen monomer", as used herein, means a DNA sequence which encodes a collagen monomer that is a component of a fibrillar collagen and which lacks the N propeptide domain, the SSAD, or both. cDNAs encoding fibrillar collagen monomers have been identified, cloned and sequenced, and are readily available to the research community through Genbank and other DNA sequence depositories. Due to the large size of the collagen monomers, the primary source of sequence information is cloned DNA sequence. By conceptual translation, the amino acid sequence of the fibrillar collagen monomers can be deduced. A DNA encoding a fibrillar collagen monomer is any DNA sequence that encodes the amino acid sequence of a fibrillar collagen monomer. Due to the degeneracy of the DNA code, a large number of different DNA sequences will be useful for the expression of any given fibrillar collagen monomer. Additionally, due to codon usage bias, the DNAs useful in the instant invention may be selected to be particularly advantageous for use in particular host cell (e.g., for use in *S. cerevisiae*, DNAs encoding fibrillar collagen monomers may be selected or synthesized which utilize codons that are preferred in *S. cerevisiae*).

The terms "defined media" or "defined medium", as used herein, means a medium for the culture of recombinant host cells which does not contain cell or tissue extracts (e.g., yeast extract, casamino acids) or serum. A defined medium normally contains vitamins, minerals, trace metals, amino acids, a carbon source, a nitrogen source, and may optionally contain a pH buffering system. If the defined medium is for use with higher eukaryotic cells, then the defined medium may also contain hormones, peptide growth factors and other proteins necessary for cell survival and growth.

A "semi-defined" medium is a medium which does not contain any unmodified animal or cell derived components. For example, a semi-defined medium may contain casamino acids, but not serum or conditioned medium.

DNA encoding any collagen monomer that is a component of fibrillar collagen may be useful in the methods of the instant invention. Particularly preferred collagen monomers are α1(I), α2(I), α1(II), α1(III), α1(V), α2(V), α3(V), α1(XI), α2(XI), and α3(XI), more preferably the human forms of α1(I), α2(I), α1(II), α1(III), α1(V), α2(V), α3(V), α1(XI), α2(XI), and α3(XI). The amino acid sequences for these proteins are available to the public (see, for example, Tromp et al., 1988, *Biochem J.* 253(3):919–922; Kuivaniemi et al., 1988, *Biochem J.* 252(3):633–640; Su et al., 1989, *Nucleic Acid Res.* 17(22):9473; Ala-Kokko et al., 1989, *Biochem. J.* 260(2):509–516; Takahara et al., 1991, *J. Biol. Chem.* 266(20):13124–13129; Weil et al., 1987, *Nucleic Acid Res.* 15(1):181–198; Bernard et al., 1988, *J. Biol. Chem.* 263(32):17159–17166; Kimura et al., 1989, *J. Biol. Chem.* 264(23):13910–13916; Mann et al., 1992, *Biol. Chem. Hoppe Seyler* 373:69–75; Sandell et al., 1991, *J. Cell. Biol.*, 114:1307–1319). Additionally, deletion mutants of fibrillar collagens such as that described in Sieron et al. (1993, *J. Biol. Chem.* 268(28):21232–21237) and D period deletions such as described in Zafarullah et al. (1997, *Matrix Biol.* 16:245–253) and Arnold et al. (1997, *Matrix Biol.* 16:105–116) may also be produced by the method of the instant invention. The DNAs may be obtained by any method from any source known in the art, such as isolation from cDNA or genomic libraries, chemical synthesis, or amplification from any available template. Additionally, DNAs encoding variants may be produced by de novo synthesis or by modification of an existing DNA by any of the methods known in the art.

DNA encoding fibrillar collagen monomers for use in accordance with the instant invention lack sequences encoding the N propeptide, the C propeptide SSAD, or both. Lees et al. (1997, supra) teach that the SSAD domain is required for proper chain selection and association of collagen monomers. Preferably, DNAs encoding fibrillar collagen monomers lack the SSAD and also lack sequence encoding at least 50% of the total C propeptide domain, more preferably at least 75% of the total C propeptide domain, and even more preferably total 90% of the propeptide domain, and most preferably DNAs encoding fibrillar collagen monomers lack all of the C propeptide domain. Alternately, the DNA encoding fibrillar collagen monomers may lack sequence encoding part or all of the N propeptide domain. Preferred deletions of the sequence encoding the N propeptide domain include DNAs lacking sequence encoding 50%, 75%, 90% or all of the N propeptide. Additionally, DNA encoding fibrillar collagen monomers may lack sequence encoding portions of or the entirety of the N and C propeptides. Preferably, the DNA encoding fibrillar collagens for use in accordance with the instant invention lack sequences encoding both the N and C propeptides. The boundaries of the mature peptide and the N and C propeptides are well known in the art.

DNA encoding fibrillar collagen monomers and non-fibrillar collagen monomers are useful for the production of gelatin in accordance with the instant invention. DNA encoding human collagen monomer(s) is preferred for the production of gelatin. As for fibrillar collagen monomers, the sequences of non-fibrillar collagens are also well known to those of skill in the art, and may be obtained using conventional techniques such as library screening, polymerase chain reaction amplification, or chemical synthesis. The DNA for use in production of gelatin in accordance with the invention is preferably lacking 50%, 75%, 90% or all of the sequence encoding the N propeptide and/or 50%, 75%, 90% or all of the sequence encoding the C propeptide. Preferably, DNA encoding collagen monomers for use in production of gelatin lacks sequence encoding both the N and C propeptides.

For use in the instant invention, the DNA encoding a fibrillar collagen monomer or a non-fibrillar collagen monomer is cloned into an expression construct. General techniques for nucleic acid manipulation useful for the practice of the claimed invention are described generally, for example, in Sambrook et al., *MOLECULAR CLONING: A LABORATORY MANUAL*, Vols. 1–3 (Cold Spring Harbor Laboratory Press, 2 ed., (1989); or F. Ausubel et al., *CURRENT PROTOCOLS IN MOLECULAR BIOLOGY* (Green Publishing and Wiley-Interscience: New York, 1987) and periodic updates.

The exact details of the expression construct will vary according to the particular host cell that is to be used as well as to the desired characteristics of the expression system, as is well known in the art. For example, for production in *S. cerevisiae*, the DNA encoding a fibrillar collagen monomer or non-fibrillar collagen monomer is placed into operable linkage with a promoter that is operable in *S. cerevisiae* and which has the desired characteristics (e.g., inducible/ derepressible or constituitive). Where bacterial host cells are utilized, promoters and promoter/operators such as the araB, trp, lac, gal, tac (a hybrid of the trp and lac promoter/ operator), T7, and the like are useful in accordance with the instant invention. Acceptable promoters for use in the instant invention where the host cell is *S. cerevisiae* include, but are not limited to GAL1-10, PHO5, PGK1, GDP1, PMA1, MET3, CUP1, GAP, TPI, MFα1 and MFα2, as well as the hybrid promoters PGK/α2, TPI/α2, GAP/GAL, PGK/GAL,, GAP/ADH2, GAP/PHO5, ADH2/PHO5, CYC1/GRE, and PGK/ARE, and other promoters active in *S. cerevisiae* as are known in the art. Where *S. pombe* is utilized as the host cell, promoters such as FBP1, NMT1, ADH1 and other promoters active in *S. pombe* as are known in the art, such as the human cytomegalovirus (hCMV) LTR. The AOX1 promoter is preferred when *Pichia pastoris* is the host cell, although other promoters known in the art, such as GAP and PGK are also acceptable. Further guidance with regard to features of expression constructs for yeast host cells may be found in, for example, Romanos et al. (1992, *Yeast* 8:423–488). When other eukaryotic cells are the desired host cell, any promoter active in the host cell may be utilized. For example, when the desired host cell is a mammalian cell line, the promoter may be a viral promoter/enhancer (e.g, the herpes virus thymidine kinase (TK) promoter or a simian virus promoter (e.g, the SV40 early or late promoter) or a long terminal repeat (LTR), such as the LTR from cytomegalovirus (CMV), Rous sarcoma virus (RSV) or mouse mammary tumor virus (MMTV)) or a mammalian promoter, preferably an inducible promoter such as the metallothionein or glucocorticoid receptor promoters and the like.

Expression constructs may also include other DNA sequences appropriate for the intended host cell. For example, expression constructs for use in higher eukaryotic cell lines (e.g., vertebrate and insect cell lines) will include a poly-adenylation site and may include an intron (including signals for processing the intron), as the presence of an intron appears to increase mRNA export from the nucleus in many systems. Additionally, a secretion signal sequence operable in the host cell is normally included as part of the construct. The secretion signal sequence may be from a collagen monomer gene or from a non-collagen gene. In one preferred embodiment, the secretion signal sequence is a prepro sequence derived from human serum albumin which contains a KEX2 protease processing site (MKWVTFISLLFLFSSAYSRGVFRR (SEQ ID NO:11) in single letter amino acid code, the signal peptidase site is between S and R, RGVF is derived from the HSA pro domain). If the secretion signal sequence is derived from a collagen monomer gene, it may be from a fibrillar collagen monomer (and may be derived from the same protein as the DNA encoding the fibrillar collagen monomer to be expressed or from a different fibrillar collagen monomer) or a non-fibrillar collagen monomer. Where the expression construct is intended for use in a prokaryotic cell, the expression construct may include a signal sequence which directs transport of the synthesized peptide into the periplasmic space or expression may be directed intracellularly.

Preferably, the expression construct will also comprise a means for selecting for host cells which contain the expression construct (a "selectable marker"). Selectable markers are well known in the art. For example, the selectable marker may be a resistance gene, such as a antibiotic resistance gene (e.g., the neo$^r$ gene which confers resistance to the antibiotic gentamycin), or it may be a gene which complements an auxotrophy of the host cell. If the host cell is a yeast cell, the selectable marker is preferably a gene which complements an auxotrophy of the cell (for example, complementing genes useful in *S. cerevisiae, P. pastoris* and *S. pombe* include LEU2, TRP1, TRP1d, URA3, URA3d, HIS3, HIS4, ARG4, LEU2d), although antibiotic resistance markers such as SH BLE, which confers resistance to ZEOCIN®, may also be used. If the host cell is a prokaryotic or higher eukaryotic cell, the selectable marker is preferably an antibiotic resistance marker (e.g., neo$^r$ or bla). Alternately, a separate selectable marker gene is not included in the expression vector, and the host cells are screened for the expression product of the DNA encoding the fibrillar collagen monomer (e.g., upon induction or derepression for controllable promoters, or after transfection for a constitutive promoter, fluorescence-activated cell sorting, FACS, may be used to select those cells which express the recombinant collagen). Preferably, the expression construct comprises a separate selectable marker gene.

The expression construct may also contain sequences which act as an "ARS" (autonomous replicating sequence) which will allow the expression construct to replicate in the host cell without being integrated into the host cell chromosome. Origins of replication for bacterial plasmids are well known. ARS for use in yeast cells are also well known (the 2$\mu$ origin of replication and operative fragments thereof, especially the full length sequence 2$\mu$ is preferred, see, for example International Patent Application No. WO 97/14431, although CEN-based plasmids and YACS are also useful in the instant invention) and ARS which act in higher mammalian cells have been recently described (see, for example, Pelletier et al., 1997, *J. Cell. Biochem.* 66(1) :87–97)). Alternately, the expression construct may include DNA sequences which will direct or allow the integration of the construct into the host cell chromosome by homologous or site-directed recombination.

Where the host cell is a eukaryotic cell, it may be advantageous for the expression vector to be a "shuttle vector", because manipulation of DNA is substantially more convenient in bacterial cells. A shuttle vector is one which carries the necessary signals to for manipulations in bacteria as well as the desired host cell. So, for example, the expression construct may also comprise an ARS ("ori") which acts in prokaryotic cells as well as a selectable marker which is useful for selection of prokaryotic cells.

The host cells for use in the instant invention may be any convenient host cell, including bacterial, yeast, and eukaryotic cells. Yeast and higher eukaryotic cells are preferred host cells. For yeast host cells, *Saccharomyces cerevisiae, Pichia pastoris, Hansenula polymorpha, Kluyveromyces lactis, Schwanniomyces occidentis, Schizosaccharomyces pombe* and *Yarrowia lipolytica* strains are preferred. Of the higher eukaryotic cells, insect cells such as Sf9 are preferred, as are mammalian cell lines which produce non-fibrillar collagens and do not produce any endogenous fibrillar collagens, such as HT-1080, 293, and NSO cells.

If the host cell does not have prolyl-4-hydroxylase activity (or has insufficient activity as is the case in insect cells), the host cell may be altered to produce prolyl-4-hydroxylase, although this is not necessary for collagen production in yeast per se, as the inventors have found that prolyl-4-hydroxylase is not required for the efficient recombinant production of collagen in yeast. However, because hydroxyproline residues contribute to the thermal stability of the collagen triple helix, it may be desirable to produce collagen in a host cell with sufficient prolyl-4-hydroxylase activity. This may be conveniently accomplished by introducing expression constructs coding for the expression of the subunits of prolyl-4-hydroxylase into the host cell. Prolyl-4-hydroxylase is a tetramer comprising two alpha subunits and two beta subunits ($\alpha 2\beta 2$). The beta subunit is also known as protein disulfide isomerase (PDI). Expression constructs for prolyl-4-hydroxylase have been described for yeast (Vuorela et al., 1997, *EMBO J* 16(22):6702–6712) and for insect cells (Lamberg et al., 1996, *J. Biol. Chem.* 271(20):11988–11995). In the case of a bacterial host cell, the expression construct for prolyl-4-hydroxylase will preferably incorporate a translocation signal to direct the transport of the subunits of the enzyme to the periplasmic space. Alternately, the prolyl-4-hydroxylase expression construct may be included in the fibrillar collagen monomer construct. In this arrangement, the expression construct may direct the production of separate messages for the fibrillar collagen monomer and the prolyl-4-hydroxylase subunits or it may direct the production of a polycistronic message. Separate messages are preferred for eukaryotic hosts, while the expression of a polycistronic message is preferred for prokaryotic hosts.

Alternately, the collagen produced in accordance with the invention may be produced in non-hydroxylated form. Non-hydroxylated fibrillar collagen has reduced thermal stability compared to hydroxylated fibrillar collagen. Fibrillar collagen with reduced thermal stability may be desirable for certain uses. However, non-hydroxylated (as well as hydroxylated collagen) may be modified to increase thermal stability by chemical modification such as, for example, chemical crosslinking.

The expression construct is introduced into the host cells by any convenient method known to the art. For example, for yeast host cells, the construct may be introduced by electroporation, lithium acetate/PEG and other methods known in the art. Higher eukaryotes may be transformed by electroporation, microprojectile bombardment, calcium phosphate transfection, lipofection, or any other method known to the art. Bacterial host cells may be transfected by electroporation, calcium chloride-mediated transfection, or any other method known in the art.

After introduction of the expression construct into the host cell, host cells comprising the expression construct are normally selected on the basis of the selectable marker that is included in the expression vector. As will be apparent, the exact details of the selection process will depend on the identity of the selectable marker. If the selectable marker is an antibiotic resistance gene, the transfected host cell population is generally cultured in the presence of an antibiotic to which resistance is conferred by the selectable marker. The antibiotic eliminates those cells which are not resistant (i.e., those cells which do not carry the resistance gene) and allows the propagation of those host cells which carry the resistance gene (and presumably carry the rest of the expression construct as well). If the selectable marker is a gene which complements an auxotrophy of the host cells, then the transfected host cell population is cultured in the absence of the compound for which the host cells are auxotrophic. Those cells which are able to propagate under these conditions carry the complementing gene to supply this compound and thus presumably carry the rest of the expression construct.

Host cells which pass the selection process may be "cloned" according to any method known in the art that is appropriate for the host cell. For microbial host cells such as yeast and bacteria, the selected cells may be plated on solid media under selection conditions, and single clones may be selected for further selection, characterization or use. Higher eukaryotic cells are generally further cloned by limiting dilution (although physical isolation methods such as micromanipulation or "cloning rings" may also be used). This process may be carried out several times to ensure the stability of the expression construct within the host cell.

For production of trimeric collagen, the recombinant host cells comprising the expression construct are generally cultured to expand cell numbers. This expansion process may be carried out in any appropriate culturing apparatus known to the art. For yeast and bacterial cells, an apparatus as simple as a shaken culture flask may be used, although large scale culture is generally carried out in a fermenter. For insect cells, the culture is generally carried out in "spinner flasks" (culture vessels comprising a means for stirring the cells suspended in a liquid culture medium). For mammalian cell lines, the cells may be grown in simple culture plates or flasks, but as for the yeast and bacterial host cells, large scale culture is generally performed in a specially adapted apparatus, a variety of which are known in the art.

The culture medium used for culture of the recombinant host cells will depend on the identity of the host cell. Culture media for the various host cells used for recombinant culture are well known in the art. The culture medium generally comprises inorganic salts and compounds, amino acids, carbohydrates, vitamins and other compounds which are either necessary for the growth of the host cells or which improve the health and/or growth of the host cells (e.g., protein growth factors and hormones where the host cells are mammalian cell lines). Semi-defined media and defined media are preferred for use in the instant invention.

Where the host cells are yeast cells, the inventors have identified media formulations which utilize no animal-derived components, such as casamino acids, that are advantageous for the production of collagen in accordance with the invention. Preferred media include media with a defined "base" medium (such as YNB) that is supplemented with specific amino acids. Preferred amino acids for supplementation include arginine, glutamate, lysine, and α-ketoglutarate. Where the defined media is supplemented with α-ketoglutarate, the media is preferably buffered to an initial acid pH, preferably about pH 5.5 to 6.5, more preferably about pH 6.0 as the pH of the media at the beginning of the culture.

If the host cells comprise (either naturally or by introduction of the appropriate expression constructs) prolyl-4-hydroxylase, then vitamin C (ascorbic acid or one of its salts) may be added to the culture medium, although applicants have found ascorbate may not be necessary if the recombinant host cells are S. cerevisiae cells. If ascorbic acid is added, it is generally added to a concentration of between 10–200 μg/ml, preferably about 80 μg/ml. If ascorbate is to be added, it need not be added until the host cells begin producing recombinant collagen.

The recombinant host cells are cultured under conditions appropriate for the expression of the DNA encoding the fibrillar collagen monomer. If the expression construct utilizes a controllable expression system, the expression of the DNA encoding the fibrillar collagen monomers is induced or derepressed, as is appropriate for the particular expression construct. The exact method of inducing or derepressing the expression of the DNA encoding the fibrillar collagen monomers will depend on the properties of the particular expression construct used and the identity of the host cell, as will be apparent to one of skill in the art. Generally, for inducible promoters, a molecule which induces expression is added to the culture medium. For example, in yeast transfected with an expression vector utilizing the GAL1-10 promoter, galactose is added to the culture medium in the absence or presence of dextrose, depending on the yeast strain utilized. In bacteria utilizing an expression vector with the lac promoter, isopropyl-β-D-thiogalactopyranoside (IPTG) is added to the medium to derepress expression. For constitutive promoters, the cells are cultured in a medium providing the appropriate environment and sufficient nutrients to support the survival of the cells and the synthesis of the fibrillar collagen monomers.

It should be noted that for production of trimeric collagen, host cells which do not produce active prolyl-4-hydroxylase should be induced at reduced temperatures (e.g., about 15–25° C., more preferably about 20° C.), to avoid thermal denaturation of the unhydroxylated trimeric fibrillar collagen. Production gelatin in host cells which do not produce active prolyl-4-hydroxylase may be accomplished at higher induction temperatures (e.g., about 26–37° C., preferably about 30° C.).

Mature fibrillar collagen is produced by the recombinant host cells. Surprisingly, the fibrillar collagen monomers assemble into mature collagen trimers in the absence of the C propeptide.

Fibrillar collagen may then be recovered from the culture. The exact method of recovery of the collagen from the culture will depend on the host cell type and the expression construct. In many microbial host cells, the collagen will be trapped within the cell wall of the recombinant host cell, even though it has been transported out of the cytoplasm. In this instance, the host cells are preferably disrupted to recover the fibrillar collagen. Alternately, cell walls may be removed or weakened to release fibrillar collagen located in the periplasm. Disruption may be accomplished by any means known in the art, including sonication, microfluidization, lysis in a french press or similar apparatus, disruption by vigorous agitation/milling with glass beads, or lysis of osmotically fragile mutant yeast strains (Broker, 1994, *Biotechniques* 16:604–615) and the like. Where the collagen is recovered by lysis or disruption of the recombinant host cells, the lysis or disruption is preferably carried out in a buffer of sufficient ionic strength to allow the collagen to remain in soluble form (e.g., more than 0.1 M NaCl, and less than 4.0 M total salts including the buffer). Alternately, in higher eukaryotic cells or microbial cells having mutations which render the cell wall "leaky", the fibrillar collagen may be recovered by collection of the culture medium.

When DNAs encoding collagen monomers lacking the N and C propeptides are utilized in yeast or prokaryotic cells in accordance with the methods of the instant invention, non-glycosylated trimeric collagen having genuine N and C terminal ends (i.e., the N and C telopeptide ends found in fibrillar collagens secreted from mammalian cells that normally produce fibrillar collagen) is produced.

Recovered collagen may be further purified. As with recovery, the method of purification will depend on the host cell type and the expression construct. Generally, recovered collagen solutions are clarified (if the collagen is recovered by cell disruption or lysis). Clarification is generally accomplished by centrifugation, but may also be accomplished by sedimentation and/or filtration if desired. The collagen-containing solution may also be delipidated when the collagen solution contains substantial amounts of lipids (such as when the collagen is recovered by cellular lysis or disruption). Delipidation may be accomplished by the use of an adsorbant such as diatomaceous earth or diatomite such as that sold as CELITE® 512. When diatomaceous earth or diatomite is utilized for delipidation, it is preferably pre-washed before use, then removed from the delipidated solution by filtration.

Collagen purification may be accomplished by any purification technique(s) known in the art. Collagen solubility can be manipulated by alterations in buffer ionic strength and pH. Collagen can be induced to: precipitate at high ionic strengths; dissolve in acidic solutions; form fibrils (by assembly of trimeric monomers) in low ionic strength buffers near neutral pH (i.e., about pH 6 to 8), thereby eliminating proteins which do not precipitate at high ionic strength; resolubilize in acidic solutions; and become insoluble in low ionic strength buffers, respectively. Any one of these manipulations may be used, singly or in combination with others to purify collagen of the invention. Additionally, solubilized collagen may be purified using any conventional purification techniques known in the art, including gel filtration chromatography, ion exchange chromatography (generally cation exchange chromatography to adsorb the collagen to the matrix, although anion exchange chromatography may also be used to remove a contaminant from the collagen-containing solution), affinity chromatography, hydrophobic interaction chromatography, and high performance liquid chromatography (Miller et al., 1982, *Meth. Enzymol.* 82:33–64).

Preferably, collagen produced in accordance with the present invention will be purified using a combination of purification techniques, such as precipitation, solubilization and ion exchange chromatography followed by fibril formation.

Recovered or purified collagen may be treated to produce gelatin. Recombinant collagen produced in accordance with the invention may be converted to gelatin by any technique known in the art, such as thermal denaturation, acid treatment, alkali treatment, or any combination thereof. Alternately, gelatin may be produced essentially directly by expression of collagen monomers in recombinant host cells lacking prolyl-4-hydroxylase activity at temperatures sufficiently high so as to denature the monomers as they are produced (e.g., about 26–37° C., more preferably about 30° C.).

After purification, collagen of the invention may be modified to modulate its properties. Crosslinking can improve the thermal stability of trimeric fibrillar collagen, especially if the collagen is nonhydroxylated collagen. Methods for crosslinking collagen are known in the art, and are disclosed, for example, in McPherson et al. (1986, *J. Biomed. Mat. Res.* 20:79–92). In general, the collagen is resuspended in a buffered solution such as phosphate buffered saline at about 3 mg/ml, and mixed with a relatively low concentration of glutaraldehyde, preferably about 0.0025–1% (v/v), more preferably 0.004–0.0075%. Preferably, the glutaraldehyde is of high purity and contains relatively low amounts of glutaraldehyde polymer. Glutaraldehyde polymer absorbs 235 nm light strongly, and so a ratio of absorbances at 280 and 235 nm can be used to assess the purity of glutaraldehyde preparations. Preferably, the glutaraldehyde has a 280 nm:235 nm ratio of about 1.8 to 2.0.

The collagen/glutaraldehyde mixture is incubated to allow crosslinking to occur. Preferably, the mixture is incubated at reduced temperature (i.e., less than about 20° C.), preferably from about 4° C. to about 18° C., with preferred temperatures being about 15° C. to about 17° C. The crosslinks stabilize the collagen fibers against thermal denaturation of the triple helix, thereby maintaining the proteolytic resistance and structural integrity of the trimeric collagen.

The patents, patent applications, and publications cited throughout the disclosure are incorporated herein by reference in their entirety.

EXAMPLES

Example 1

Recombinant Production of Type I Telopeptide Collagen

Figure 7:
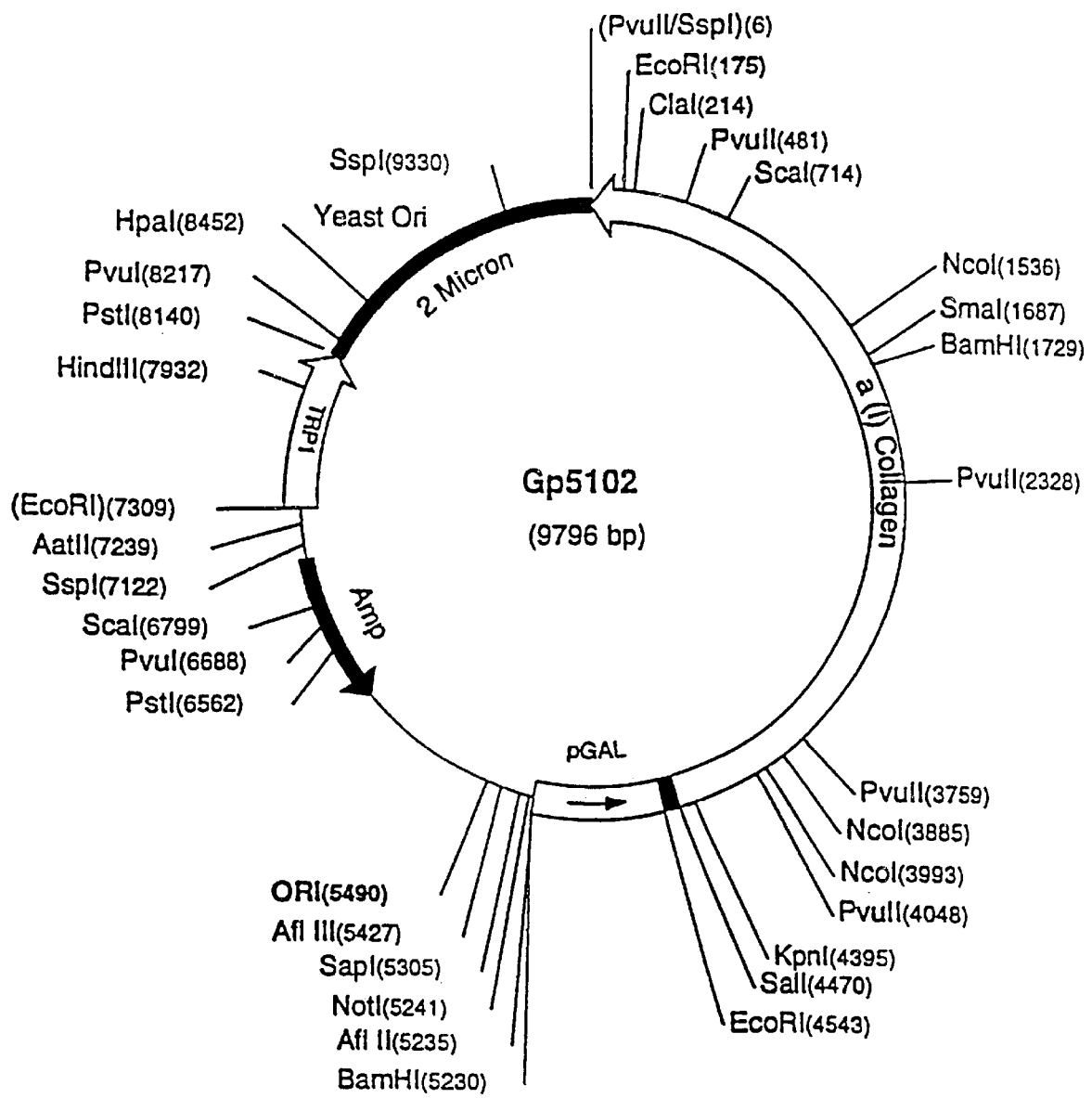
FIG. 7 shows a map of shuttle vector plasmid Gp5102.
Figure 8:
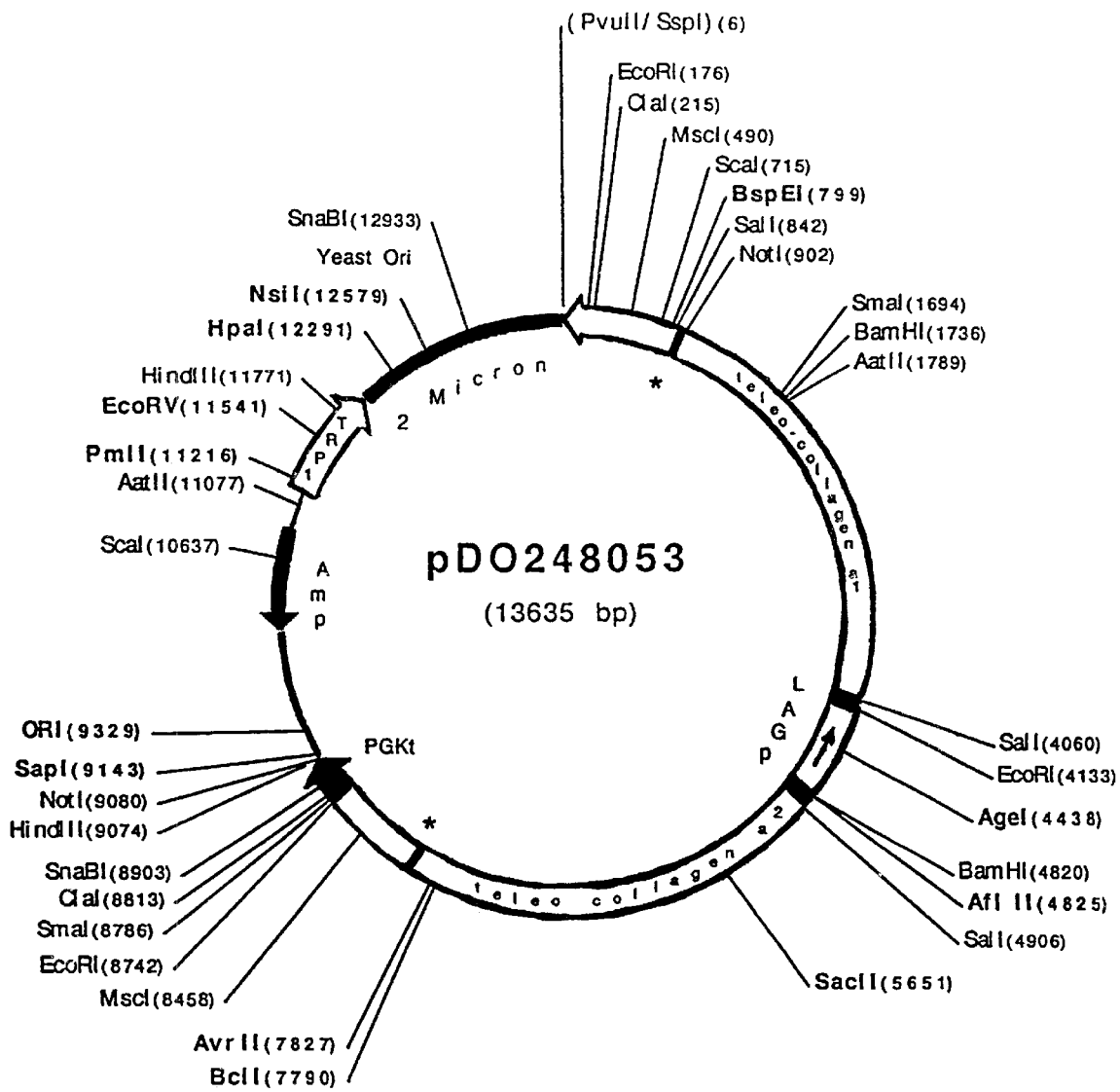
FIG. 8 shows a map of the shuttle vector plasmid pDO248053. The "*" marks the location of the stop sequence TAATGA at the ends of the C telopeptides.

Recombinant type I telopeptide collagen (α1 homotrimer and α1/α2 heterotrimer) was produced in *S. cerevisiae* host cells using expression constructs coding for human α1(I) and α2(I) collagen monomers. A number of different shuttle vectors were created, most based on Gp5432 (see FIG. 2 for a map of Gp5432) which contains DNA encoding the preprocollagen α1(I) and α2(I) monomers operably linked to the bidirectional GAL1-10 promoter (the sequences of preproα1(I) and preproα2(I) are shown in FIGS. 3 and 4, respectively). The PGK terminator (PGKt) is supplied at the 3' end of the α2(I) sequence, while a terminator in the 2μ DNA (from the FLP gene) acts to terminate transcription of the α1(I) gene. Gp5432 also contains a yeast selectable marker (TRP1), an operable 1.6 kb fragment of the 2μ yeast origin, a bacterial ori, and a bacterial selectable marker (bla). Additionally, a construct was made based on Gp5102, which is very similar to Gp5432 but does not contain the α2(I) sequence or the PGKt (see FIG. 7 for a map of Gp5102). Constructs were created from Gp5432 which: (a) replaced the collagen secretion signal sequence (the "pre" domain) with a prepro domain from human serum albumin (HSA) which additionally contains a KEX2 protease processing site (MKWVTFISLLFLFSSAYSRGVFRR in single letter amino acid code (the KEX2 protease cleaves at the carboxy-end of RR), designated pGET462); (b) encoded pC α1(I) and pC α2(I) linked to the preproHSA/KEX2 protease recognition sequence (designated pDO243880); and (c) and constructs with the α1(I) and α2(I) mature domain (i.e., the signal sequence and the N and C propeptides were deleted from the preproCOL1A1 and preproCOL1A2) linked to the preproHSA/KEX2 protease recognition sequence or their native signal sequences (designated pDO248053 and pDO248098, respectively). pDO248010 was created from Gp5102, and encodes the α1(I) telopeptide sequence linked to the preproHSA/KEX2 protease recognition sequence.

The expression constructs were transformed into GY5361 by electroporation. This host strain also contained a chromosomally-integrated expression construct encoding for the two subunits of chicken prolyl-4-hydroxylase. The alpha subunit (Bassuk et al., 1989, *Proc. Natl. Acad Sci. USA* 86:7382–7386) and beta subunit, also known as PDI (Kao et al., 1988, *Conn. Tiss. Res.* 18:157–174), were cloned into an expression construct under the control of the bidirectional GAL1-10 promoter. The prolyl-4-hydroxylase construct also included the URA3 selectable marker and sequences from the TRP1 gene to allow integration by homologous recombination. Correct integrants were trp1⁻.

After electroporation of GY5361 with 100 ng of plasmid DNA, transformants were selected on 2% agar plates containing 2% dextrose, 0.67% yeast nitrogen base lacking amino acids (YNB), 0.5% casamino acids by growing 3 days at 30° C. Transformants were grown overnight at 30° C. in media containing 2% dextrose, 0.67% YNB, 0.5% casamino acids to an $OD_{600}$ of 3 (approximately $1 \times 10^8$ cells/ml). To induce collagen expression, the overnight cultures (in glucose-containing media) were dilute to $OD_{600}$ of approximately 0.05 in media containing 0.5% galactose, 0.5% dextrose, 0.67% YNB and 0.5% casamino acids, 1% sodium citrate, pH 6.5, 50 mM sodium ascorbate, 300 mM α-ketoglutarate, 100 mM ferric chloride ($FeCl_3$), 100 mM glycine, 100 mM proline. Inductions were allowed to proceed for 48–96 hours at 30° C.

Cells were harvested by centrifugation, resuspended in 0.1 M Tris HCl, pH 7.4, 0.4 M NaCl, 10 mM EDTA and lysed by vortexing in a centrifuge tube with glass beads. The beads and cellular debris were removed by centrifugation. Production of type I collagen was measured by immunoassay and protease sensitivity.

Collagen yield was determined using a luminometric immunoassay. The assay utilizes a goat anti-type I collagen antibody commercially available from Biodesign International (Kennebunk, Me.) derivatized with either biotin or ruthenium chelate. Samples were diluted from 1:40 to 1:60 in "Matrix buffer" (100 mM PIPES, pH 6.8, and 1% w/v bovine serum albumin) and 25 μl samples were dispensed into tubes. 50 μl of an antibody working solution containing 1 μg/ml of ruthenium chelate conjugated antibody and 1.5 μg/ml biotin conjugated antibody in diluent (Matrix buffer plus 1.5% Tween-20) was added to each tube and the tubes were incubated for two hours at room temperature (approximately 20° C.). After the incubation, 25 μl of a 1 mg/ml solution of streptavidin-conjugated magnetic beads (in diluent) were added to each tube. The tubes were shaken or vortexed for 30 seconds. 200 μl of assay buffer (ORIGEN assay buffer, Igen, Inc., catalog number 402-050-01) was added to each tube and the tubes were mixed then placed in a ORIGEN analyzer (Igen, Inc., model #1100-1000). Total protein was determined using the BCA assay (Pierce) according the manufacturer's instructions. Results are shown below in Table 1.

TABLE 1

| Strain | Proteins encoded | Expression levels (μg collagen/ mg protein) |
|---|---|---|
| CYT 30 | preproCOLα1(I)/preproCOLα2(I) | 0.68 ± 0.046 |
| CYT 31 | preproHSAproα1(I)/preproHSAproα2(I) | 0.43 ± 0.015 |
| CYT 32 | preproHSApCα1(I)/preproHSAproα2(I) | 1.21 ± 0.19 |
| CYT 33 | preproHSAα1(I)/preproHSAα2(I) | 1.50 ± 0.038 |
| CYT 44 | preCOLα1(I)/preCOLα2(I) | 0.13 ± 0.022 |

The constructs expression α1 and α2 linked to their native signal sequences gave reduced expression, which is believed to be due to an alteration of the amino acid context at the signal peptidase cleavage site, which impairs signal peptide processing.

Figure 5:
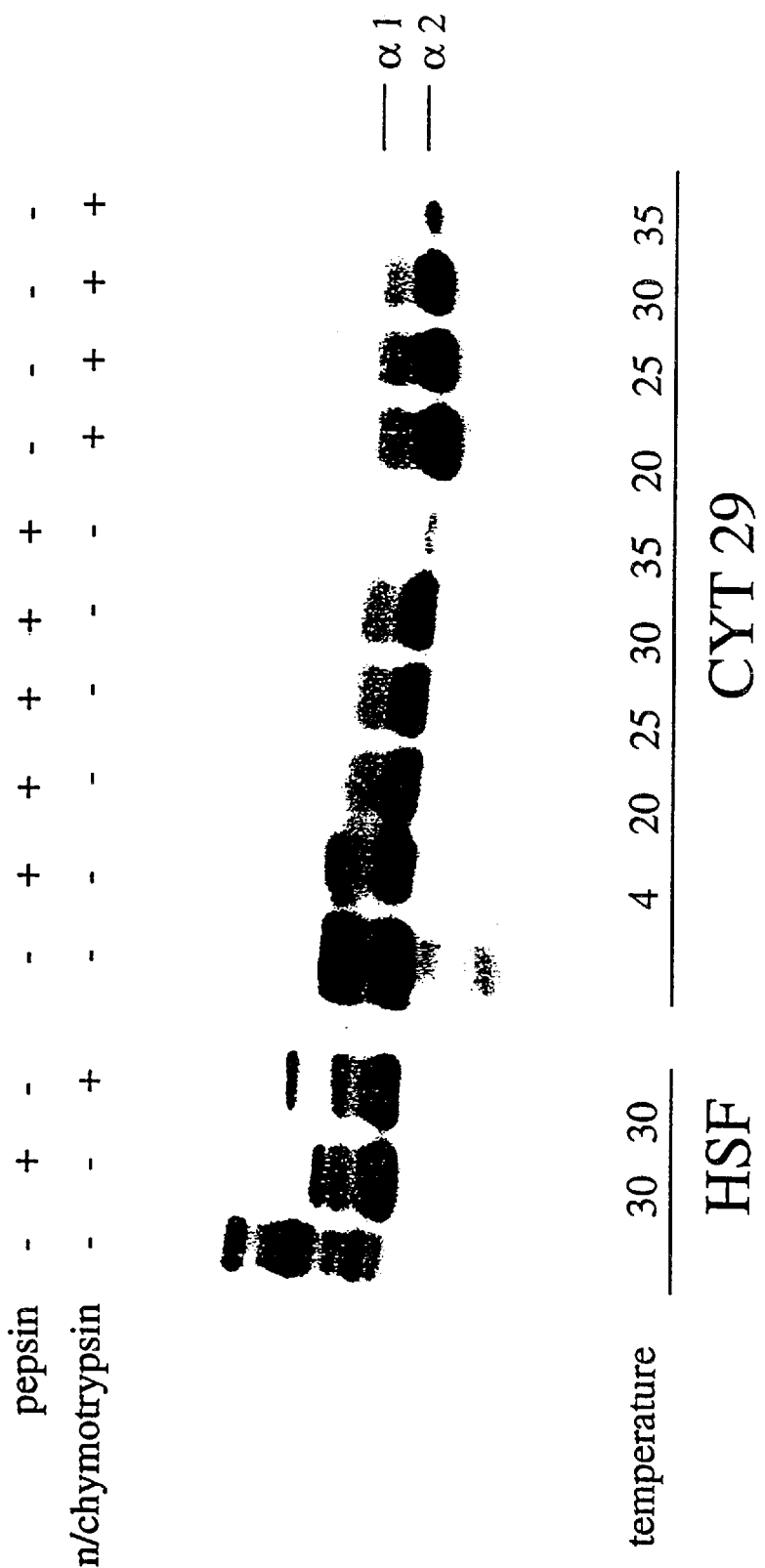
FIG. 5 shows a half-tone reproduction of a western blot demonstrating results from a thermal stability protease assay. Lanes labeled HSF are samples of type I procollagen from medium conditioned by human skin fibroblasts. Lanes labeled CYT29 (strain GY5344 transformed with pDO248053) are collagen produced in yeast using an expression construct encoding preproHSAα1(I) and preproHSAα2(I) (preproHSAα1(I) and preproHSAα2(I) comprise the human serum albumin signal sequence plus four amino acids of the pro domain linked to a KEX2 cleavage site fused to the α1(I) and α2(I) telopeptide collagen monomers).

The collagens were also tested by proteolytic assays for thermal stability. Resistance to pepsin or trypsin/chymotrypsin was measured by the method of Bruckner et al. (1981, *Anal. Biochem.* 110:360–368). Basically, samples were incubated with protease at a series of temperatures (4, 20, 25, 30 and 35° C. for pepsin and 20, 25, 30 and 35° C. for trypsin/chymotrypsin). Type I collagen from human skin fibroblasts was incubated with pepsin or trypsin/chymotrypsin as a standard. Results were assayed by western blotting (Towbin et al., 1979, *Proc. Natl. Acad. Sci. USA* 76:4350–4354) using a rabbit anti-type I collagen antibody from Rockland, Inc. (Gilbertsville, Pa.), detected with a peroxidase-labeled goat anti-rabbit IgG (H+L) and visualized with a chemiluminescent reaction (ECL Western Blotting Kit, Amersham, Inc.). Assay results for α1(I)/α2(I) heterotrimer are shown in FIG. 5. α1(I) homotrimer had equivalent thermal stability as measured by this assay (data not shown).

In this assay, the triple helical portions of the collagen trimer are resistant to protease digestion. As the temperature is increased to the melting point of the triple helical region, the triple helical portions of the molecule become susceptible to proteolytic digestion. Monomeric collagen chains and improperly folded collagen monomers are highly susceptible to protease at low temperatures. These results show that the collagen produced by expression of DNA encoding α1(I) and α2(I) collagen lacking the N and C propeptides is approximately equivalent to human skin fibroblast type I procollagen with regards to thermal stability and protease resistance.

Figure 6:
FIG. 6 shows a half-tone reproduction of a western blot demonstrating results from a mammalian collagenase digest of human skin fibroblast and yeast-derived collagen. Lanes labeled HSF are samples of type I procollagen from human skin fibroblasts. Lanes labeled CYT29 are collagen produced in yeast using an expression construct encoding preproHSAα1(I) and preproHSAα2(I).

The correct folding and register of the three monomers in the yeast-produced triple helical collagen was assayed by digestion with mammalian collagenase. Human skin fibroblast collagenase cleaves each of the three chains of collagen at a single point. Collagenase is highly sensitive to local structure and sequence at the cleavage site. If the molecule is improperly folded or the chains are folded out of register, collagenase will not cleave (Wu et al., 1990, *Proc. Natl. Acad. Sci. USA* 78:5888–5892). Samples were digested with purified human fibroblast collagenase in 0.05 M Tris-HCl, pH 7.5, 0.15 M NaCl, 0.01 M $CaCl_2$ for 16 hours at 25° C. Prior to use in the assay, procollagenase was activated by treatment with 10 μg/ml trypsin at 25° C. for 30 minutes. The activation reaction was stopped by the addition of soybean trypsin inhibitor to a final concentration of 50 μg/ml. Results were displayed by western blotting using the same system as used for assaying protease resistance and are shown in FIG. 6. The data indicate that collagen produced by expression of DNA encoding α1(I) and α2(I) collagen lacking the N and C propeptides is correctly folded and the monomer chains are assembled in correct register.

Example 2

Construction of Host Cell Strains

Strains of *S. cerevisiae* which contain the subunits of prolyl-4-hydroxylase integrated into the TRP1 gene, a mutation in the GAL1 gene, a mutation in the LEU2 gene, and a mutation in the SUC2 gene were created for use in recombinant collagen production.

Strain YPH499a MATα ura3-52 lys2-801 ade2-101a trp1-Δ63 his3-Δ200 leu2Δ1 GAL) was crossed to strain X2180-1B (MATα SUC mal mel gal2 CUP1) to produce diploid strain GY5020. GY5020 was induced to sporulate and colonies from random spores were screened for genotypes MATα ura3-52 GAL, MATα leu2α1 GAL and MATα trp1-Δ63 ura3-52 GAL SUC. One colony of each genotype was selected and designated GY5203, SC1214, and GY 5198, respectively.

SC1214 was crossed with YM147 (MATα gal1-Δ102 ura3-52 trp1-289a, (obtained from Mark Johnston of Washington University) to produce diploid strain GY5193, which was induced to sporulate. Colonies from randomly selected spores were screened for genotypes MATα leu2Δ1 GAL and MATα leu2Δ1 ura3-52 gal1-Δ102 and designated GY5209 and GY5208, respectively.

GY5209 was crossed to GY5151 (strain 11a obtained from David Botstein of Stanford University), MATα trp1 ura3 lys2 suc2Δ gal) to produce diploid strain GY5291. GY5291 was sporulated and tetrads were dissected to isolate a colony with the genotype MATα Leu2Δ1 suc2Δ GAL, which was designated GY5357.

Strain GY5203 (MATα ura3-52 GAL+) was transformed with a linear DNA containing the genes encoding the two subunits of prolyl-4-hydroxylase (cPDI and cP4-H) under the control of pGAL1-10, the URA3 gene and sequence targeting the DNA into the TRP1 locus by homologous recombination. Integrants were selected for the presence of the URA3 allele by growth on selective media, and further selected for high levels of expression of the prolyl-4-hydroxylase subunits. A URA3 colony which produced high levels of the prolyl-4-hydroxylase subunits was streaked out, and a single colony was selected and designated GY 5344 (MATα ura3-52 GAL trp1::{cPDI cP4-H URA3}).

GY5344 was crossed to GY5357, and the resulting diploid was sporulated and analyzed by tetrad dissection. Trp⁻ colonies from tetrads containing 4 Ura⁺ segregants were selected and transformed with Gp5432. Transformants were analyzed for collagen expression. The colony which had the highest level of collagen expression after transformation with Gp5432, GY5381, was found to be MATα ura3-52 suc2Δ trp1::{cPDI, cP4-H URA3}.

GY5381 was crossed to GY5208 to yield diploid strain GY5349. GY 5349 was sporulated and the resulting tetrads were dissected. Colonies arising from individual spores were transformed with Gp5432 and analyzed for collagen expression. The colony which gave the best collagen expression after transformation with Gp5432 was designated GYT3681 (MATα ura3-52 gal1Δ102 trp1::{cPDI, cP4-H URA3}). GY5362 (MATα ura3-52 gal1-Δ102 trp1::{cPDI, cP4-H URA3} suc2Δ leu2Δ1) and GY5364 (MATα ura3-52 gal1-Δ102 trp1::{cPDI, cP4-H URA3} suc2Δ leu2Δ1) were also isolated from the tetrad dissection of GY5349.

Figure 11:
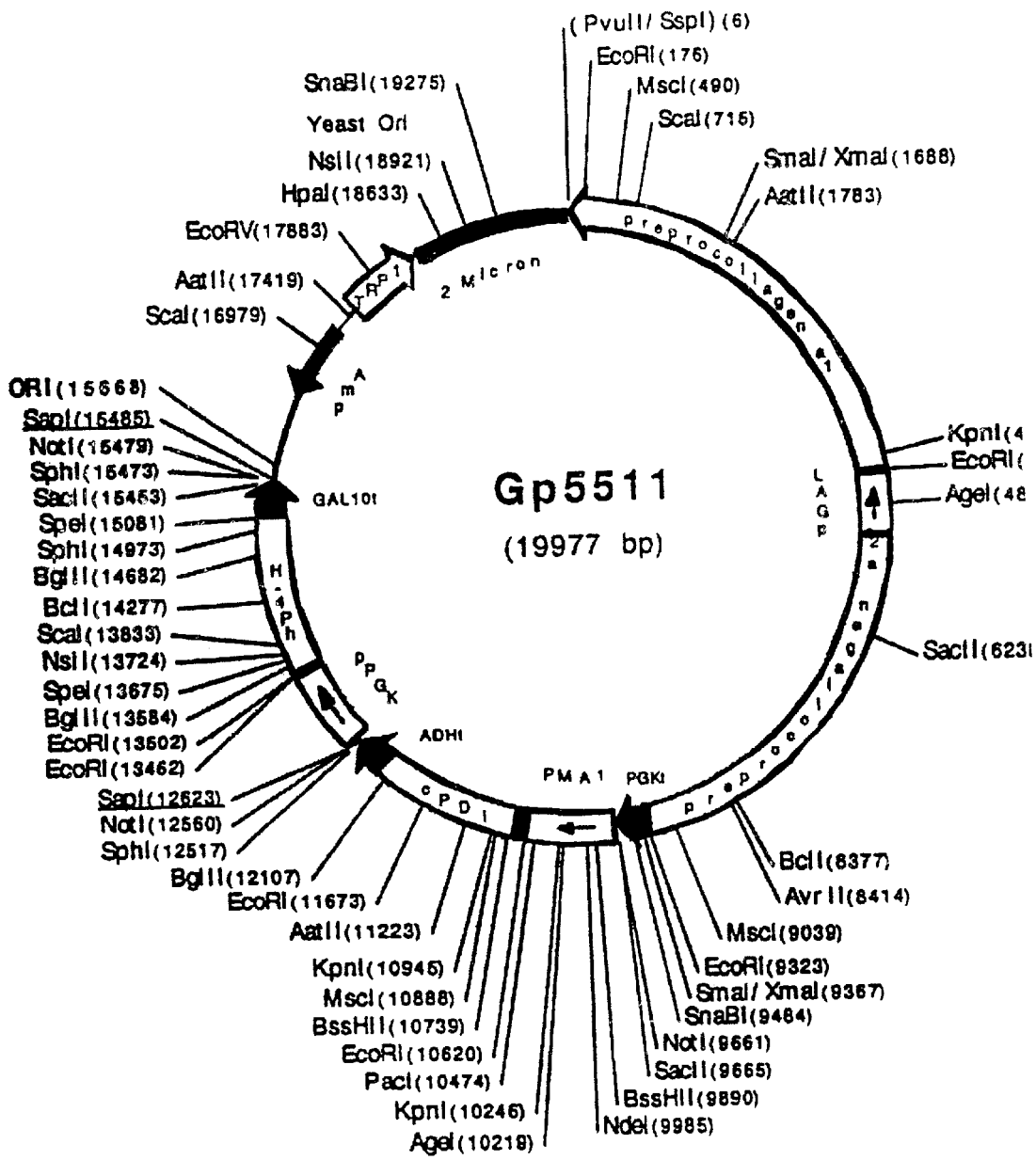
FIG. 11 shows a map of the shuttle vector plasmid Gp5511.
Figure 12:
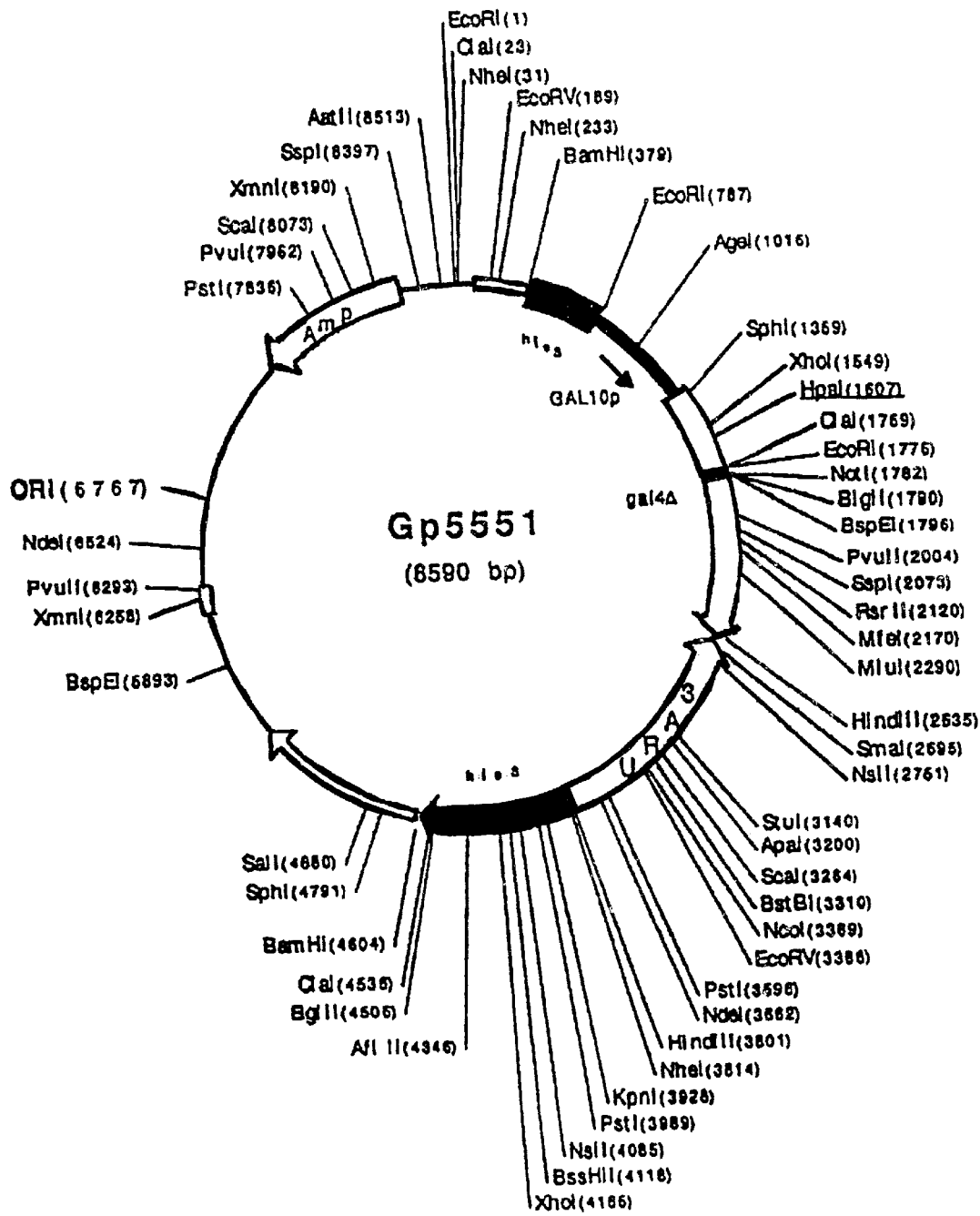
FIG. 12 shows a map of the shuttle vector plasmid Gp5551.

GY5198 was transformed with a linear DNA derived from Gp5551 (FIG. 12), which contains the gal4-mini marker, the URA3 selectable marker, and sequences targeting homologous recombination into the HIS3 locus. Transformants were selected for the presence of URA3, and screened for collagen production by transformation with Gp5511 (which carries genes encoding α1 and α2 telopeptide collagen monomers as well as the two subunits of prolyl-4-hydroxylase, and is diagrammed in FIG. 11). Strain GY5355 was selected on the basis of high collagen expression after transformation with Gp5511.

GY5362 was transformed with Gp5432 to yield GYT3683 (MATα ura3-52 gal1-Δ102 trp1::{cPDI, cP4-H URA3} suc2Δ leu2Δ1+Gp5432), which was crossed to GY5355 to generate diploid strain GYT3690. GYT3690 was induced to sporulate and analyzed by tetrad dissection. Several MATα TRP⁺ his⁻ gal⁻ colonies were analyzed with respect to procollagen expression, and the colony with the highest expression was designated GYT3728 (MATα ura3-52 gal1-α102 trp1::{cPDI cP4-h URA3} his3::{gal4-mini URA3}+Gp5432).

GYT3728 was crossed to GY5364 (MATα ura3-52 gal1-Δ102 trp1::{cPDI, cP4-H URA3} suc2Δ leu2Δ1) to yield diploid GYT3737. Tetrad dissection was performed, and colonies arising from individual spores were analyzed for procollagen production and thermal stability of the procollagen (a measure of prolyl-4-hydroxylase activity). Three strains, GYT3721 (MATα ura3-52 gal1-Δ102 trp1::{cPDI cP4-H URA3}+Gp5432), GYT3732 (MATα ura3-52 gal1-Δ102 trp1::{cPDI cP4-H URA3} suc2Δ leu2Δ1+Gp5432), and GYT3733 (MATα ura3-52 gal1-Δ102 trp1::{cPDI cP4-H URA3} suc2Δ leu2Δ1+Gp5432) were selected for high procollagen expression and high thermal stability. Thermal stability was highest in collagen produced by GYT3731.

GYT3731, GYT3732 and GYT3733 were "cured" of Gp5432 by culture in non-selective media (e.g., media containing tryptophan) followed by screening for TRP⁻ strains. One strain which retained the genotype of the parent strain (with the exception of the presence of Gp5432) was isolated for each parent, and designated GY5382 (sometimes referred to as G3), GY5379 (sometimes referred to as G95) and GY5385 (sometimes referred to as G98), respectively.

Example 3

Recombinant Collagen Production in Yeast with Defined Media

Defined media utilizing no animal-derived components were tested for use in collagen production. Strain GYT3731 (strain GY5382, described above, transformed with plasmid Gp5432) was used for these experiments.

YNB (Difco) was the base media for these experiments.

Overnight cultures of GYT3731 were grown in YNB with 2% glucose (w/v) and 0.5% casamino acids (w/v). The overnight cultures were used to inoculate 5 ml test cultures to a starting optical density (OD) of 0.1. Growth and procollagen production were assayed after a 60–65 hour incubation. The cells were collected by centrifugation, resuspended in PBS, mixed with an equal volume of acid-washed glass beads, and frozen at −70° C. The cells were thawed and lysed by vortexing for 6 minutes, then assayed by immunoassay as described in Example 1.

YNB, 2% glucose, 0.5% galactose was tested with and without 0.5% CAA or an amino acid cocktail (AA, 20 mg/L arginine HCl, 100 mg/L sodium glutamate, 20 mg/L histidine, 30 mg/L lysine HCl, 20 mg/L methionine, 50 mg/L phenylalanine, 375 mg/L serine, 20 mg/L tryptophan, 30 mg/L tyrosine, 150 mg/L valine). The cells grown in media with CAA grew to a higher final density and showed greatly enhanced procollagen production compared to YNB alone or YNB+AA. Procollagen production data is shown in Table 2.

TABLE 2

| Medium | Procollagen Production ($\mu$g/mg total protein) |
|---|---|
| YNB | 0.04 |
| YNB + 0.5% CAA | 2.48 |
| YNB + AA | 0.1 |

CAA supplementation supports a substantial improvement in procollagen production as compared to YNB alone or with the AA amino acid mixture.

Figure 9:
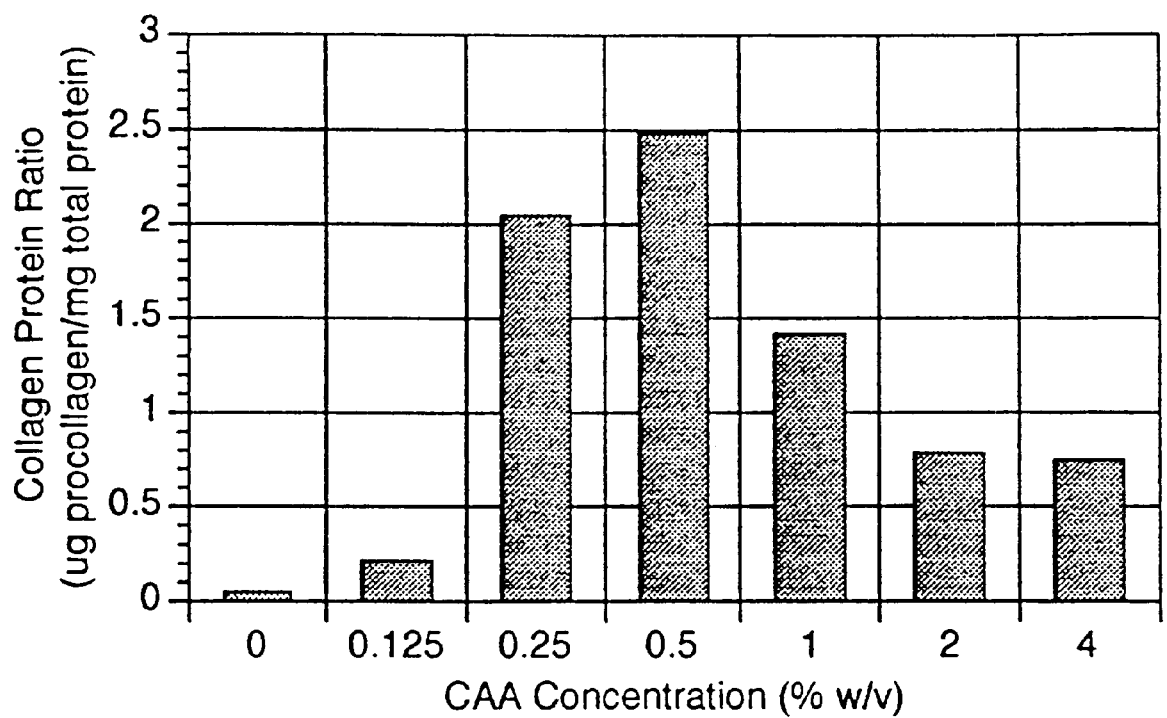
FIG. 9 shows a bar graph depicting procollagen production in different media formulations.

The optimal concentration of CAA supplementation was tested by using a range of concentrations of CAA. Results are shown in FIG. 9. 0.5% CAA supplementation supports the highest levels of procollagen production.

CAA was compared to the media supplements Bacto Tryptone® (BT), Bacto Peptone® (BP) and yeast extract (YE), utilizing the same protocol as above. Results are shown in Table 3.

TABLE 3

| Medium | Procollagen Production ($\mu$g/mg total protein) |
|---|---|
| YNB + 0.25% CAA | 2.34 |
| YNB + 0.5% CAA | 4.24 |
| YNB + 1% CAA | 1.54 |
| YNB + 0.25% BT | 1.92 |
| YNB + 0.5% BT | 1.81 |
| YNB + 1% BT | 1.14 |
| YNB + 0.25% BP | 0.76 |
| YNB + 0.5% BP | 1.15 |
| YNB + 1% BP | 1.46 |
| YNB + 0.25% YE | 1.74 |
| YNB + 0.5% YE | 2.33 |
| YNB + 1% YE | 1.53 |
| YNB | 0.26 |

CAA is an animal-derived product. Such products are disadvantageous for production of materials for medical use, due to regulatory issues. Since CAA appears to be the most stimulatory for procollagen production, simpler amino acid mixtures, based on the concentrations that would be found in medium containing 0.5% CAA (which are significantly higher levels than previously used for the AA cocktail used in the experiments described in Table 2) were made and tested to identify the stimulatory component(s). YNB was supplemented with RQK (110 mg/L arginine HCl, 765 mg/L sodium glutamate and 286 mg/L lysine HCl), Q (1534 mg/L sodium glutamate), or $\alpha$K (3063 mg/L disodium $\alpha$-ketoglutarate). Results are shown in Table 4.

TABLE 4

| Medium | Procollagen Production ($\mu$g/mg total protein) |
|---|---|
| YNB + 0.5% CAA | 3.64 (n = 3) |
| YNB + RQK | 3.71 |
| YNB + Q | 3.44 |
| YNB + $\alpha$K | 3.32 |

All three amino acid supplements supported procollagen expression levels approximately equal to that of YNB+0.5% CAA.

The effect of pH on the effectiveness of the $\alpha$K supplement was tested. YNB was supplemented with $\alpha$-ketoglutarate to 1534 mg/L, and tested without added pH buffer or with $PO_4$ (50 mM sodium phosphate, pH 7.0), Succ (50 mM sodium succinate, pH 6.5) or Cit (1% sodium citrate (47.6 mM), pH 6.0) buffer. Results are shown in Table 5.

TABLE 5

| Medium | Procollagen Production ($\mu$g/mg total protein) | Final pH |
|---|---|---|
| YNB + $\alpha$K | 1.11 | 2.77 |
| YNB + $\alpha$k/$PO_4$ | 1.75 | 5.36 |
| YNB + $\alpha$k/Succ | 2.23 | 5.30 |
| YNB + $\alpha$K/Cit | 3.12 | 5.41 |

Decreased pH appears to increase procollagen production in defined media supplemented with $\alpha$-ketoglutarate.

Example 4 pN and pC Collagen Production in Yeast

Constructs were created to express four different triple helical type I collagens: procollagen, pN collagen, pC collagen, and collagen lacking both the N and C propeptides (telopeptide collagen). The expression constructs were based on plasmid Gp5432 and included sequences encoding both the $\alpha$1(I) and $\alpha$2(I) monomers. Each construct contained a heterologous prepro sequence (from the HSA gene, as described in Example 1).

Each construct was transformed into strain GY5382, described above in Example 2. A colony from each transformation was selected, and the strains were designated CYT 89 (procollagen), CYT 87 (pN collagen), CYT 90 (pC collagen) and CYT 59 (telopeptide collagen).

Each strain was grown in YNB buffered with 1% sodium citrate, pH 6.5, and supplemented with 10 g/L glucose, 5 g/L galactose, 0.5% casamino acids. Each culture was grown at 30° C. and harvested at 100 hours. Collagen production was assayed as described above in Example 1. Assay results are shown in Table 6.

TABLE 6

| Medium | Collagen Production ($\mu$g/mg total protein) |
|---|---|
| CYT 89 (procollagen) | 1.64 |
| CYT 87 (pN collagen) | 6.45 |
| CYT 90 (pC collagen | 9.7 |
| CYT 59 (telopeptide collagen) | 29.8 |

Example 5

Production of Hydroxylated Telocollagen in Yeast Cells

Strain CYT59 (strain GY5382 transformed with pDO248053) was cultured in a yeast fermentation apparatus for ~120 hours. The recombinant yeast were collected by centrifugation from six liters of fermentation broth and chilled to 8° C. (all subsequent steps were performed at 8° C. unless otherwise noted). The pelleted cells were resuspended in four liters of 0.1 M Tris-HCl, 0.4 M NaCl, pH 7.4, and lysed by passing the cell suspension through a Dyno- Mill KDL Special containing 500 grams of acid-washed glass beads at a flow rate of 75 ml/minute. The resulting lysate was centrifuged at 16,000×g for 1 hour to remove cellular debris. The clarified lysate was delipidated by the addition of 80 grams of CELITE® 512 followed by stirring for one hour. The mixture was then filtered in two passes through Whatman GF/F glass fiber filter (0.7 μm) with Whatman GF/D as a prefilter to remove the Celite and any other insoluble material.

Collagen was precipitated from the clarified, delipidated solution by the addition of NaCl crystals to the solution to make it 3.9 M in NaCl, followed by gentle mixing overnight. The precipitated collagen was collected by centrifugation, then washed by resuspension in 0.1 M Tris-HCl, pH 7.4, 3.5 M NaCl followed by centrifugation. The pelleted collagen was resuspended in 0.1 M Tris-HCl, pH 7.4 with stirring overnight. The resuspended collagen solution was clarified by centrifugation, then dialyzed against 100 volumes of 50 mM sodium acetate, pH 4.5. A precipitate formed during dialysis which was removed by centrifugation at 26,000×g for one hour. The supernatant was passed over a 250 ml SP-SEPHAROSE® column which had been equilibrated in 50 mM sodium acetate, pH 4.5. The column was washed with 50 mM sodium acetate, then eluted in a single step with 50 mM sodium acetate, pH 4.5, 0.45 M NaCl. The eluted material was concentrated by ultrafiltration using an Amicon stirred cell under positive pressure and a YM-10 membrane. The concentrated collagen was then precipitated by making the solution 1.2 M in NaCl, 10 mM HCl. The precipitate was collected by centrifugation at 26,000×g for one hour and resuspended in 10 mM HCl at a concentration of 3 mg/ml. The acidified collagen solution was dialyzed against 100 volumes of 20 mM sodium phosphate, pH 7.2, at 15° C., overnight.

Figure 10:
FIG. 10 shows a transmission electron micrograph of recombinant collagen fibrils.

A suspension of collagen fibers was diluted 20 mM sodium phosphate, pH 7.2, to a final collagen concentration of 0.25–0.5 mg/ml, and transferred to thin bar, high definition square 400 mesh copper grids (Polysciences, Inc.), washed, and dried in a dessicator overnight. The grids were negatively stained with 1% phosphotungstic acid, pH 7. The grids were examined and photographed in a Joel 1200EX transmission electron microscope operating at 80 kV. A photomicrograph of recombinant collagen fibers (30,000× magnification) is shown in FIG. 10. The fibrils display the characteristic banding pattern of collagen fibrils.

The present invention has been detailed both by direct description and by example. Equivalents and modifications of the present invention will be apparent to those skilled in the art, and are encompassed within the scope of the invention.

We claim:

1. A method for the production of fibrillar collagen comprising:
   culturing a recombinant host cell comprising a DNA encoding a fibrillar collagen monomer lacking a C propeptide SSAD under conditions appropriate for expression of said DNA; and
   producing fibrillar collagen.

2. The method of claim 1 wherein said DNA encodes a fibrillar collagen monomer lacking at least 50% of the C propeptide.

3. The method of claim 2 wherein said DNA encodes a fibrillar collagen monomer lacking at least 75% of the C propeptide.

4. The method of claim 3 wherein said DNA encodes a fibrillar collagen monomer lacking at least 90% of the C propeptide.

5. The method of claim 4 wherein said DNA encodes a fibrillar collagen monomer lacking the C propeptide.

6. The method of claim 1 wherein said DNA encodes a fibrillar collagen lacking a C propeptide SSAD and lacking a N propeptide.

7. The method of claim 1 wherein said DNA encodes a fibrillar collagen selected from the group consisting of collagen α1(I), collagen α2(I), collagen α1(III), collagen α1(V), collagen α2(V), collagen α3(V), collagen α1(XI), collagen α2(XI), and collagen α3(XI).

8. The method of claim 5 wherein said DNA encodes a fibrillar collagen selected from the group consisting of collagen α1(I), collagen α2(I), collagen α1(III), collagen α1(V), collagen α2(V), collagen α3(V), collagen α1(XI), collagen α2(XI), and collagen α3(XI).

9. The method of claim 1 wherein said DNA is operably linked to a second DNA sequence encoding a heterologous prepro sequence.

10. The method of claim 9 wherein said heterologous prepro sequence is a human serum albumin prepro sequence.

11. The method of claim 1 wherein said host cell is a yeast cell.

12. The method of claim 11 wherein said host cell is a *Saccharomyces cerevisiae* cell.

13. The method of claim 11 wherein said host cell is a *Pichia pastoris* cell.

14. The method of claim 1 wherein said host cell is an insect cell.

15. The method of claim 1 wherein said host cell is a bacterial cell.

16. The method of claim 15 wherein said host cell is an *Escherichia coli* cell.

17. The method of claim 1 wherein said host cell is a mammalian cell line.

18. The method of claim 17 wherein said host cell is a HT-1080 cell.

19. The method of claim 11 wherein said host cell is cultured in defined media.

20. The method of claim 19 wherein said defined media comprises at least one amino acid selected from the group consisting of arginine, glutamic acid, lysine and α-ketoglutarate.

21. The method of claim 20 wherein said defined media comprises arginine, glutamic acid and lysine, but no other amino acids.

22. The method of claim 20 wherein said defined media comprises a pH buffer which buffers the defined media to about pH 5.5 to about pH 7.0.

23. The method of claim 22 wherein said defined media comprises a pH buffer which buffers the defined media to about pH 6.0.

24. The method of claim 1 wherein said host cell comprises DNA encoding active prolyl-4-hydroxylase.

25. The method of claim 1 wherein said host cell does not comprise DNA encoding active prolyl-4-hydroxylase.

26. A method for the production of fibrillar procollagen, comprising:
    culturing a recombinant yeast host cell comprising a DNA encoding a fibrillar collagen monomer lacking a N propeptide under conditions appropriate for expression of said DNA; and
    producing fibrillar collagen.

27. The method of claim 26 wherein said DNA comprises sequence encoding a fibrillar collagen monomer lacking a N-propeptide linked to a non-collagen signal sequence.

28. A recombinant host cell comprising:
    an expression construct comprising DNA encoding a fibrillar collagen monomer lacking a C propeptide SSAD.

29. A method of producing telopeptide collagen fibrils, comprising:
    culturing a recombinant host cell comprising a DNA encoding a fibrillar collagen monomer lacking a C propeptide and a N propeptide under conditions appropriate for expression of said DNA, thereby producing fibrillar collagen;
    recovering said fibrillar collagen; and
    forming fibrils from said fibrillar collagen.

30. The method of claim 29 wherein said method further comprises purifying said recovered fibrillar collagen.

31. A method of producing gelatin, comprising culturing a recombinant host cell comprising a DNA encoding a collagen monomer lacking a N or C propeptide under conditions appropriate for expression of said DNA; and
    producing gelatin.

* * * * *

SEQUENCE LISTING

```
<160> NUMBER OF SEQ ID NOS: 11

<210> SEQ ID NO 1
<211> LENGTH: 23
<212> TYPE: PRT
<213> ORGANISM: Homo sapiens

<400> SEQUENCE: 1

Gly Gly Gln Gly Ser Asp Pro Ala Asp Val Ala Ile Gln Leu Thr Phe
 1               5                  10                  15

Leu Arg Leu Met Ser Thr Glu
            20

<210> SEQ ID NO 2
<211> LENGTH: 23
<212> TYPE: PRT
<213> ORGANISM: Homo sapiens

<400> SEQUENCE: 2

Asn Val Glu Gly Val Thr Ser Lys Glu Met Ala Thr Gln Leu Ala Phe
 1               5                  10                  15

Met Arg Leu Leu Ala Asn Tyr
            20

<210> SEQ ID NO 3
<211> LENGTH: 23
<212> TYPE: PRT
<213> ORGANISM: Homo sapiens

<400> SEQUENCE: 3

Gly Asp Asp Asn Leu Ala Pro Asn Thr Ala Asn Val Gln Met Thr Phe
 1               5                  10                  15

Leu Arg Leu Leu Ser Thr Glu
            20
```

<210> SEQ ID NO 4
<211> LENGTH: 23
<212> TYPE: PRT
<213> ORGANISM: Homo sapiens

<400> SEQUENCE: 4

Phe Asn Pro Glu Leu Pro Glu Asp Val Leu Asp Val Gln Leu Ala Phe
 1               5                  10                  15

Leu Arg Leu Leu Ser Ser Arg
            20

<210> SEQ ID NO 5
<211> LENGTH: 22
<212> TYPE: PRT
<213> ORGANISM: Homo sapiens

<400> SEQUENCE: 5

Val Asp Ala Glu Phe Asn Pro Val Gly Val Val Gln Met Thr Gly Leu
 1               5                  10                  15

Arg Leu Leu Ser Ala Ser
            20

<210> SEQ ID NO 6
<211> LENGTH: 22
<212> TYPE: PRT
<213> ORGANISM: Homo sapiens

<400> SEQUENCE: 6

Gly Asp His Gln Ser Pro Asn Thr Ala Ile Thr Gln Met Thr Phe Leu
 1               5                  10                  15

Arg Leu Leu Ser Lys Glu
            20

<210> SEQ ID NO 7
<211> LENGTH: 22
<212> TYPE: PRT
<213> ORGANISM: Homo sapiens

<400> SEQUENCE: 7

Leu Asp Val Glu Gly Asn Ser Ile Asn Met Val Gln Met Thr Phe Leu
 1               5                  10                  15

Lys Leu Leu Thr Ala Ser
            20

<210> SEQ ID NO 8
<211> LENGTH: 22
<212> TYPE: PRT
<213> ORGANISM: Homo sapiens

<400> SEQUENCE: 8

Val Asp Ser Glu Gly Ser Pro Val Gly Val Val Gln Leu Thr Phe Leu
 1               5                  10                  15

Arg Leu Leu Ser Val Ser
            20

<210> SEQ ID NO 9
<211> LENGTH: 1461
<212> TYPE: PRT
<213> ORGANISM: Homo sapiens

<400> SEQUENCE: 9

Met Phe Ser Phe Val Asp Leu Arg Leu Leu Leu Leu Leu Ala Ala Thr

-continued

```
  1               5                  10                 15
Ala Leu Leu Thr His Gly Gln Glu Gly Gln Val Glu Gly Gln Asp
             20              25             30

Glu Asp Ile Pro Pro Ile Thr Cys Val Gln Asn Gly Leu Arg Tyr His
         35              40             45

Asp Arg Asp Val Trp Lys Pro Glu Pro Cys Arg Ile Cys Val Cys Asp
     50              55             60

Asn Gly Lys Val Leu Cys Asp Asp Val Ile Cys Asp Glu Thr Lys Asn
 65              70             75                       80

Cys Pro Gly Ala Glu Val Pro Gly Glu Cys Cys Pro Val Cys Pro
                 85              90              95

Asp Gly Ser Glu Ser Pro Thr Asp Gln Glu Thr Thr Gly Val Glu Gly
             100             105            110

Asp Thr Gly Pro Arg Gly Pro Arg Gly Pro Ala Gly Pro Pro Gly Arg
         115             120            125

Asp Gly Ile Pro Gly Gln Pro Gly Leu Pro Gly Pro Pro Gly Pro Pro
     130             135            140

Gly Pro Pro Gly Pro Pro Gly Leu Gly Gly Asn Phe Ala Pro Gln Leu
145             150             155                      160

Ser Tyr Gly Tyr Asp Glu Lys Ser Thr Gly Ile Ser Val Pro Gly
                 165             170            175

Pro Met Gly Pro Ser Gly Pro Arg Gly Leu Pro Gly Pro Pro Gly Ala
             180             185            190

Pro Gly Pro Gln Gly Phe Gln Gly Pro Pro Gly Glu Pro Gly Glu Pro
         195             200            205

Gly Ala Ser Gly Pro Met Gly Pro Arg Gly Pro Pro Gly Pro Pro Gly
     210             215            220

Lys Asn Gly Asp Asp Gly Glu Ala Gly Lys Pro Gly Arg Pro Gly Glu
225             230             235                      240

Arg Gly Pro Pro Gly Pro Gln Gly Ala Arg Gly Leu Pro Gly Thr Ala
                 245             250            255

Gly Leu Pro Gly Met Lys Gly His Arg Gly Phe Ser Gly Leu Asp Gly
             260             265            270

Ala Lys Gly Asp Ala Gly Pro Ala Gly Pro Lys Gly Glu Pro Gly Ser
         275             280            285

Pro Gly Glu Asn Gly Ala Pro Gly Gln Met Gly Pro Arg Gly Leu Pro
     290             295            300

Gly Glu Arg Gly Arg Pro Gly Ala Pro Gly Pro Ala Gly Ala Arg Gly
305             310             315                      320

Asn Asp Gly Ala Thr Gly Ala Ala Gly Pro Pro Gly Pro Thr Gly Pro
                 325             330            335

Ala Gly Pro Pro Gly Phe Pro Gly Ala Val Gly Ala Lys Gly Glu Ala
             340             345            350

Gly Pro Gln Gly Pro Arg Gly Ser Glu Gly Pro Gln Gly Val Arg Gly
         355             360            365

Glu Pro Gly Pro Pro Gly Pro Ala Gly Ala Ala Gly Pro Ala Gly Asn
     370             375            380

Pro Gly Ala Asp Gly Gln Pro Gly Ala Lys Gly Ala Asn Gly Ala Pro
385             390             395                      400

Gly Ile Ala Gly Ala Pro Gly Phe Pro Gly Ala Arg Gly Pro Ser Gly
                 405             410            415

Pro Gln Gly Pro Gly Gly Pro Pro Gly Pro Lys Gly Asn Ser Gly Glu
             420             425            430
```

```
Pro Gly Ala Pro Gly Ser Lys Gly Asp Thr Gly Ala Lys Gly Glu Pro
            435                 440                 445
Gly Pro Val Gly Val Gln Gly Pro Gly Pro Ala Gly Glu Glu Gly
450                 455                 460
Lys Arg Gly Ala Arg Gly Glu Pro Gly Pro Thr Gly Leu Pro Gly Pro
465                 470                 475                 480
Pro Gly Glu Arg Gly Gly Pro Gly Ser Arg Gly Phe Pro Gly Ala Asp
                485                 490                 495
Gly Val Ala Gly Pro Lys Gly Pro Ala Gly Glu Arg Gly Ser Pro Gly
            500                 505                 510
Pro Ala Gly Pro Lys Gly Ser Pro Gly Glu Ala Gly Arg Pro Gly Glu
            515                 520                 525
Ala Gly Leu Pro Gly Ala Lys Gly Leu Thr Gly Ser Pro Gly Ser Pro
            530                 535                 540
Gly Pro Asp Gly Lys Thr Gly Pro Pro Gly Pro Ala Gly Gln Asp Gly
545                 550                 555                 560
Arg Pro Gly Pro Pro Gly Pro Pro Gly Ala Arg Gly Gln Ala Gly Val
                565                 570                 575
Met Gly Phe Pro Gly Pro Lys Gly Ala Ala Gly Glu Pro Gly Lys Ala
            580                 585                 590
Gly Glu Arg Gly Val Pro Gly Pro Pro Gly Ala Val Gly Pro Ala Gly
            595                 600                 605
Lys Asp Gly Glu Ala Gly Ala Gln Gly Pro Pro Gly Pro Ala Gly Pro
            610                 615                 620
Ala Gly Glu Arg Gly Glu Gln Gly Pro Ala Gly Ser Pro Gly Phe Gln
625                 630                 635                 640
Gly Leu Pro Gly Pro Ala Gly Pro Pro Gly Glu Ala Gly Lys Pro Gly
                645                 650                 655
Glu Gln Gly Val Pro Gly Asp Leu Gly Ala Pro Gly Pro Ser Gly Ala
                660                 665                 670
Arg Gly Glu Arg Gly Phe Pro Gly Glu Arg Gly Val Gln Gly Pro Pro
            675                 680                 685
Gly Pro Ala Gly Pro Arg Gly Ala Asn Gly Ala Pro Gly Asn Asp Gly
            690                 695                 700
Ala Lys Gly Asp Ala Gly Ala Pro Gly Ala Pro Gly Ser Gln Gly Ala
705                 710                 715                 720
Pro Gly Leu Gln Gly Met Pro Gly Glu Arg Gly Ala Ala Gly Leu Pro
                725                 730                 735
Gly Pro Lys Gly Asp Arg Gly Asp Ala Gly Pro Lys Gly Ala Asp Gly
            740                 745                 750
Ser Pro Gly Lys Asp Gly Val Arg Gly Leu Thr Gly Pro Ile Gly Pro
            755                 760                 765
Pro Gly Pro Ala Gly Ala Pro Gly Asp Lys Gly Glu Ser Gly Pro Ser
770                 775                 780
Gly Pro Ala Gly Pro Thr Gly Ala Arg Gly Ala Pro Gly Asp Arg Gly
785                 790                 795                 800
Glu Pro Gly Pro Pro Gly Pro Ala Gly Phe Ala Gly Pro Pro Gly Ala
                805                 810                 815
Asp Gly Gln Pro Gly Ala Lys Gly Glu Pro Gly Asp Ala Gly Ala Lys
            820                 825                 830
Gly Asp Ala Gly Pro Pro Gly Pro Ala Gly Pro Ala Gly Pro Pro Gly
            835                 840                 845
```

```
Pro Ile Gly Asn Val Gly Ala Pro Gly Ala Lys Gly Ala Arg Gly Ser
    850                 855                 860
Ala Gly Pro Pro Gly Ala Thr Gly Phe Pro Gly Ala Ala Gly Arg Val
865                 870                 875                 880
Gly Pro Pro Gly Pro Ser Gly Asn Ala Gly Pro Pro Gly Pro Pro Gly
                885                 890                 895
Pro Ala Gly Lys Glu Gly Gly Lys Gly Pro Arg Gly Glu Thr Gly Pro
            900                 905                 910
Ala Gly Arg Pro Gly Glu Val Gly Pro Pro Gly Pro Pro Gly Pro Ala
            915                 920                 925
Gly Glu Lys Gly Ser Pro Gly Ala Asp Gly Pro Ala Gly Ala Pro Gly
        930                 935                 940
Thr Pro Gly Pro Gln Gly Ile Ala Gly Gln Arg Gly Val Val Gly Leu
945                 950                 955                 960
Pro Gly Gln Arg Gly Glu Arg Gly Phe Pro Gly Leu Pro Gly Pro Ser
                965                 970                 975
Gly Glu Pro Gly Lys Gln Gly Pro Ser Gly Ala Ser Gly Glu Arg Gly
            980                 985                 990
Pro Pro Gly Pro Met Gly Pro Pro Gly Leu Ala Gly Pro Pro Gly Glu
            995                1000                1005
Ser Gly Arg Glu Gly Ala Pro Gly Ala Glu Gly Ser Pro Gly Arg Asp
 1010                1015                1020
Gly Ser Pro Gly Ala Lys Gly Asp Arg Gly Glu Thr Gly Pro Ala Gly
1025                1030                1035                1040
Pro Pro Gly Ala Pro Gly Ala Pro Val Ala Pro Gly Pro Val Gly Pro
                1045                1050                1055
Ala Gly Lys Ser Gly Asp Arg Gly Glu Thr Gly Pro Ala Gly Pro Ala
            1060                1065                1070
Gly Pro Val Gly Pro Val Gly Ala Arg Gly Pro Ala Gly Pro Gln Gly
            1075                1080                1085
Pro Arg Gly Asp Lys Gly Glu Thr Gly Glu Gln Gly Asp Arg Gly Ile
        1090                1095                1100
Lys Gly His Arg Gly Phe Ser Gly Leu Gln Gly Pro Pro Gly Pro Pro
1105                1110                1115                1120
Gly Ser Pro Gly Glu Gln Gly Pro Ser Gly Ala Ser Gly Pro Ala Gly
                1125                1130                1135
Pro Arg Gly Pro Pro Gly Ser Ala Gly Ala Pro Gly Lys Asp Gly Leu
            1140                1145                1150
Asn Gly Leu Pro Gly Pro Ile Gly Pro Pro Gly Pro Arg Gly Arg Thr
            1155                1160                1165
Gly Asp Ala Gly Pro Val Gly Pro Pro Gly Pro Pro Gly Pro Pro Gly
        1170                1175                1180
Pro Pro Gly Pro Pro Ser Ala Gly Phe Asp Phe Ser Phe Leu Pro Gln
1185                1190                1195                1200
Pro Pro Gln Glu Lys Ala His Asp Gly Gly Arg Tyr Tyr Arg Ala Asp
                1205                1210                1215
Asp Ala Asn Val Val Arg Asp Arg Asp Leu Glu Val Asp Thr Thr Leu
            1220                1225                1230
Lys Ser Leu Ser Gln Gln Ile Glu Asn Ile Arg Ser Pro Glu Gly Ser
            1235                1240                1245
Arg Lys Asn Pro Ala Arg Thr Cys Arg Asp Leu Lys Met Cys His Ser
 1250                1255                1260
Asp Trp Lys Ser Gly Glu Tyr Trp Ile Asp Pro Asn Gln Gly Cys Asn
```

```
                                       1265                  1270                  1275                  1280
Leu Asp Ala Ile Lys Val Phe Cys Asn Met Glu Thr Gly Glu Thr Cys
                1285                  1290                  1295

Val Tyr Pro Thr Gln Pro Ser Val Ala Gln Lys Asn Trp Tyr Ile Ser
           1300                  1305                  1310

Lys Asn Pro Lys Asp Lys Arg His Val Trp Phe Gly Glu Ser Met Thr
           1315                  1320                  1325

Asp Gly Phe Gln Phe Glu Tyr Gly Gly Gln Gly Ser Asp Pro Ala Asp
           1330                  1335                  1340

Val Ala Ile Gln Leu Thr Phe Leu Arg Leu Met Ser Thr Glu Ala Ser
1345                  1350                  1355                  1360

Gln Asn Ile Thr Tyr His Cys Lys Asn Ser Val Ala Tyr Met Asp Gln
                1365                  1370                  1375

Gln Thr Gly Asn Leu Lys Lys Ala Leu Leu Leu Lys Gly Ser Asn Glu
           1380                  1385                  1390

Ile Glu Ile Arg Ala Glu Gly Asn Ser Arg Phe Thr Tyr Ser Val Thr
           1395                  1400                  1405

Val Asp Gly Cys Thr Ser His Thr Gly Ala Trp Gly Lys Thr Val Ile
           1410                  1415                  1420

Glu Tyr Lys Thr Thr Lys Thr Ser Arg Leu Pro Ile Ile Asp Val Ala
1425                  1430                  1435                  1440

Pro Leu Asp Val Gly Ala Pro Asp Gln Glu Phe Gly Phe Asp Val Gly
                1445                  1450                  1455

Pro Val Cys Phe Leu
           1460

<210> SEQ ID NO 10
<211> LENGTH: 1366
<212> TYPE: PRT
<213> ORGANISM: Homo sapiens

<400> SEQUENCE: 10

Met Leu Ser Phe Val Asp Thr Arg Thr Leu Leu Leu Leu Ala Val Thr
 1               5                  10                  15

Leu Cys Leu Ala Thr Cys Gln Ser Leu Gln Glu Glu Thr Val Arg Lys
                20                  25                  30

Gly Pro Ala Gly Asp Arg Gly Pro Arg Gly Glu Arg Gly Pro Pro Gly
           35                  40                  45

Pro Pro Gly Arg Asp Gly Glu Asp Gly Pro Thr Gly Pro Pro Gly Pro
           50                  55                  60

Pro Gly Pro Pro Gly Pro Pro Gly Leu Gly Gly Asn Phe Ala Ala Gln
65                  70                  75                  80

Tyr Asp Gly Lys Gly Val Gly Leu Gly Pro Gly Pro Met Gly Leu Met
                85                  90                  95

Gly Pro Arg Gly Pro Pro Gly Ala Ala Gly Ala Pro Gly Pro Gln Gly
                100                 105                 110

Phe Gln Gly Pro Ala Gly Glu Pro Gly Glu Pro Gly Gln Thr Gly Pro
           115                 120                 125

Ala Gly Ala Arg Gly Pro Ala Gly Pro Pro Gly Lys Ala Gly Glu Asp
           130                 135                 140

Gly His Pro Gly Lys Pro Gly Arg Pro Gly Glu Arg Gly Val Val Gly
145                 150                 155                 160

Pro Gln Gly Ala Arg Gly Phe Pro Gly Thr Pro Gly Leu Pro Gly Phe
                165                 170                 175
```

-continued

```
Lys Gly Ile Arg Gly His Asn Gly Leu Asp Gly Leu Lys Gly Gln Pro
            180                 185                 190
Gly Ala Pro Gly Val Lys Gly Glu Pro Gly Ala Pro Gly Glu Asn Gly
            195                 200                 205
Thr Pro Gly Gln Thr Gly Ala Arg Gly Leu Pro Gly Glu Arg Gly Arg
            210                 215                 220
Val Gly Ala Pro Gly Pro Ala Gly Ala Arg Gly Ser Asp Gly Ser Val
225                 230                 235                 240
Gly Pro Val Gly Pro Ala Gly Pro Ile Gly Ser Ala Gly Pro Pro Gly
            245                 250                 255
Phe Pro Gly Ala Pro Gly Pro Lys Gly Glu Ile Gly Ala Val Gly Asn
            260                 265                 270
Ala Gly Pro Ala Gly Pro Ala Gly Pro Arg Gly Glu Val Gly Leu Pro
            275                 280                 285
Gly Leu Ser Gly Pro Val Gly Pro Pro Gly Asn Pro Gly Ala Asn Gly
            290                 295                 300
Leu Thr Gly Ala Lys Gly Ala Ala Gly Leu Pro Gly Val Ala Gly Ala
305                 310                 315                 320
Pro Gly Leu Pro Gly Pro Arg Gly Ile Pro Gly Pro Val Gly Ala Ala
            325                 330                 335
Gly Ala Thr Gly Ala Arg Gly Leu Val Gly Glu Pro Gly Pro Ala Gly
            340                 345                 350
Ser Lys Gly Glu Ser Gly Asn Lys Gly Glu Pro Gly Ser Ala Gly Pro
            355                 360                 365
Gln Gly Pro Pro Gly Pro Ser Gly Glu Glu Gly Lys Arg Gly Pro Asn
            370                 375                 380
Gly Glu Ala Gly Ser Ala Gly Pro Pro Gly Pro Pro Gly Leu Arg Gly
385                 390                 395                 400
Ser Pro Gly Ser Arg Gly Leu Pro Gly Ala Asp Gly Arg Ala Gly Val
            405                 410                 415
Met Gly Pro Pro Gly Ser Arg Gly Ala Ser Gly Pro Ala Gly Val Arg
            420                 425                 430
Gly Pro Asn Gly Asp Ala Gly Arg Pro Gly Glu Pro Gly Leu Met Gly
            435                 440                 445
Pro Arg Gly Leu Pro Gly Ser Pro Gly Asn Ile Gly Pro Ala Gly Lys
            450                 455                 460
Glu Gly Pro Val Gly Leu Pro Gly Ile Asp Gly Arg Pro Gly Pro Ile
465                 470                 475                 480
Gly Pro Ala Gly Ala Arg Gly Glu Pro Gly Asn Ile Gly Phe Pro Gly
            485                 490                 495
Pro Lys Gly Pro Thr Gly Asp Pro Gly Lys Asn Gly Asp Lys Gly His
            500                 505                 510
Ala Gly Leu Ala Gly Ala Arg Gly Ala Pro Gly Pro Asp Gly Asn Asn
            515                 520                 525
Gly Ala Gln Gly Pro Pro Gly Pro Gln Gly Val Gln Gly Gly Lys Gly
            530                 535                 540
Glu Gln Gly Pro Ala Gly Pro Pro Gly Phe Gln Gly Leu Pro Gly Pro
545                 550                 555                 560
Ser Gly Pro Ala Gly Glu Val Gly Lys Pro Gly Glu Arg Gly Leu His
            565                 570                 575
Gly Glu Phe Gly Leu Pro Gly Pro Ala Gly Pro Arg Gly Glu Arg Gly
            580                 585                 590
Pro Pro Gly Glu Ser Gly Ala Ala Gly Pro Thr Gly Pro Ile Gly Ser
```

-continued

```
            595                 600                 605
Arg Gly Pro Ser Gly Pro Pro Gly Pro Asp Gly Asn Lys Gly Glu Pro
            610                 615                 620
Gly Val Gly Ala Val Gly Thr Ala Gly Pro Ser Gly Pro Ser Gly
625                 630                 635                 640
Leu Pro Gly Glu Arg Gly Ala Ala Gly Ile Pro Gly Gly Lys Gly Glu
                645                 650                 655
Lys Gly Glu Pro Gly Leu Arg Gly Glu Ile Gly Asn Pro Gly Arg Asp
                660                 665                 670
Gly Ala Arg Gly Ala His Gly Ala Val Gly Ala Pro Gly Pro Ala Gly
                675                 680                 685
Ala Thr Gly Asp Arg Gly Glu Ala Gly Ala Ala Gly Pro Ala Gly Pro
                690                 695                 700
Ala Gly Pro Arg Gly Ser Pro Gly Glu Arg Gly Glu Val Gly Pro Ala
705                 710                 715                 720
Gly Pro Asn Gly Phe Ala Gly Pro Ala Gly Ala Ala Gly Gln Pro Gly
                725                 730                 735
Ala Lys Gly Glu Arg Gly Ala Lys Gly Pro Lys Gly Glu Asn Gly Val
                740                 745                 750
Val Gly Pro Thr Gly Pro Val Gly Ala Ala Gly Pro Ala Gly Pro Asn
                755                 760                 765
Gly Pro Pro Gly Pro Ala Gly Ser Arg Gly Asp Gly Gly Pro Pro Gly
770                 775                 780
Met Thr Gly Phe Pro Gly Ala Ala Gly Arg Thr Gly Pro Pro Gly Pro
785                 790                 795                 800
Ser Gly Ile Ser Gly Pro Pro Gly Pro Pro Gly Pro Ala Gly Lys Glu
                805                 810                 815
Gly Leu Arg Gly Pro Arg Gly Asp Gln Gly Pro Val Gly Arg Thr Gly
                820                 825                 830
Glu Val Gly Ala Val Gly Pro Pro Gly Phe Ala Gly Glu Lys Gly Pro
                835                 840                 845
Ser Gly Glu Ala Gly Thr Ala Gly Pro Pro Gly Thr Pro Gly Pro Gln
                850                 855                 860
Gly Leu Leu Gly Ala Pro Gly Ile Leu Gly Leu Pro Gly Ser Arg Gly
865                 870                 875                 880
Glu Arg Gly Leu Pro Gly Val Ala Gly Ala Val Gly Glu Pro Gly Pro
                885                 890                 895
Leu Gly Ile Ala Gly Pro Pro Gly Ala Arg Gly Pro Pro Gly Ala Val
                900                 905                 910
Gly Ser Pro Gly Val Asn Gly Ala Pro Gly Glu Ala Gly Arg Asp Gly
                915                 920                 925
Asn Pro Gly Asn Asp Gly Pro Pro Gly Arg Asp Gly Gln Pro Gly His
                930                 935                 940
Lys Gly Glu Arg Gly Tyr Pro Gly Asn Ile Gly Pro Val Gly Ala Ala
945                 950                 955                 960
Gly Ala Pro Gly Pro His Gly Pro Val Gly Pro Ala Gly Lys His Gly
                965                 970                 975
Asn Arg Gly Glu Thr Gly Pro Ser Gly Pro Val Gly Pro Ala Gly Ala
                980                 985                 990
Val Gly Pro Arg Gly Pro Ser Gly Pro Gln Gly Ile Arg Gly Asp Lys
                995                 1000                1005
Gly Glu Pro Gly Glu Lys Gly Pro Arg Gly Leu Pro Gly Leu Lys Gly
    1010                1015                1020
```

-continued

His Asn Gly Leu Gln Gly Leu Pro Gly Ile Ala Gly His His Gly Asp
1025                1030                1035                1040

Gln Gly Ala Pro Gly Ser Val Gly Pro Ala Gly Pro Arg Gly Pro Ala
            1045                1050                1055

Gly Pro Ser Gly Pro Ala Gly Lys Asp Gly Arg Thr Gly His Pro Gly
        1060                1065                1070

Thr Val Gly Pro Ala Gly Ile Arg Gly Pro Gln Gly His Gln Gly Pro
    1075                1080                1085

Ala Gly Pro Pro Gly Pro Pro Gly Pro Pro Gly Pro Pro Gly Val Ser
1090                1095                1100

Gly Gly Gly Tyr Asp Phe Gly Tyr Asp Gly Asp Phe Tyr Arg Ala Asp
1105                1110                1115                1120

Gln Pro Arg Ser Ala Pro Ser Leu Arg Pro Lys Asp Tyr Glu Val Asp
            1125                1130                1135

Ala Thr Leu Lys Ser Leu Asn Asn Gln Ile Glu Thr Leu Leu Thr Pro
        1140                1145                1150

Glu Gly Ser Arg Lys Asn Pro Ala Arg Thr Cys Arg Asp Leu Arg Leu
    1155                1160                1165

Ser His Pro Glu Trp Ser Ser Gly Tyr Tyr Trp Ile Asp Pro Asn Gln
1170                1175                1180

Gly Cys Thr Met Asp Ala Ile Lys Val Tyr Cys Asp Phe Ser Thr Gly
1185                1190                1195                1200

Glu Thr Cys Ile Arg Ala Gln Pro Glu Asn Ile Pro Ala Lys Asn Trp
            1205                1210                1215

Tyr Arg Ser Ser Lys Asp Lys Lys His Val Trp Leu Gly Glu Thr Ile
        1220                1225                1230

Asn Ala Gly Ser Gln Phe Glu Tyr Asn Val Glu Gly Val Thr Ser Lys
    1235                1240                1245

Glu Met Ala Thr Gln Leu Ala Phe Met Arg Leu Leu Ala Asn Tyr Ala
1250                1255                1260

Ser Gln Asn Ile Thr Tyr His Cys Lys Asn Ser Ile Ala Tyr Met Asp
1265                1270                1275                1280

Glu Glu Thr Gly Asn Leu Lys Lys Ala Val Ile Leu Gln Gly Ser Asn
            1285                1290                1295

Asp Val Glu Leu Val Ala Glu Gly Asn Ser Arg Phe Thr Tyr Thr Val
        1300                1305                1310

Leu Val Asp Gly Cys Ser Lys Lys Thr Asn Glu Trp Gly Lys Thr Ile
    1315                1320                1325

Ile Glu Tyr Lys Thr Asn Lys Pro Ser Arg Leu Pro Phe Leu Asp Ile
1330                1335                1340

Ala Pro Leu Asp Ile Gly Gly Ala Asp His Glu Phe Phe Val Asp Ile
1345                1350                1355                1360

Gly Pro Val Cys Phe Lys
            1365

<210> SEQ ID NO 11
<211> LENGTH: 24
<212> TYPE: PRT

```
-continued

<213> ORGANISM: Artificial Sequence
<220> FEATURE:
<223> OTHER INFORMATION: Description of Artificial Sequence: Synthetic
      construct

<400> SEQUENCE: 11

Met Lys Trp Val Thr Phe Ile Ser Leu Leu Phe Leu Phe Ser Ser Ala
 1               5                  10                  15

Tyr Ser Arg Gly Val Phe Arg Arg
                20
```